United States Patent [19]
McMaster et al.

[11] Patent Number: 5,877,403
[45] Date of Patent: Mar. 2, 1999

[54] PAPAYA RINGSPOT VIRUS PROTEASE GENE

[75] Inventors: J. Russell McMaster, Galesburg; Maury L. Boeshore; David M. Tricoli, both of Kalamazoo; John F. Reynolds, Augusta; Kim J. Carney, Richland; Jerry L. Slightom, Kalamazoo, all of Mich.; Dennis Gonsalves, Geneva, N.Y.

[73] Assignees: Seminis Vegetable Seeds, Inc., Saticoy, Calif.; Cornell Research Foundation, Ithaca, N.Y.

[21] Appl. No.: 366,490

[22] Filed: Dec. 30, 1995

[51] Int. Cl.$^6$ ........................................ A01H 5/00
[52] U.S. Cl. .................. 800/205; 435/252.2; 435/252.3; 435/320.1; 435/419; 435/430; 536/23.72
[58] Field of Search .......................... 800/205; 536/23.2, 536/24.1, 23.72; 435/320.1, 172.3, 69.1, 252.3, 252.2, 419, 430

[56] References Cited

U.S. PATENT DOCUMENTS

| | | | |
|---|---|---|---|
| 5,349,128 | 9/1994 | Quemada et al. ....................... | 800/205 |
| 5,589,612 | 12/1996 | Jilka et al. ............................. | 800/205 |

OTHER PUBLICATIONS

Maureen M.M. Fitch, Richard M. Manshardt, Dennis Gonsalves, Jerry L. Slightom and John C. Sanford, Virus Resistant Papaya Plants Derived From Tissues Bombarded With The Coat Protein Gene Of Papaya Ringspot Virus, *Bio/Technology* 10:1466–1472 (Nov. 1992).
John H. Fitchen and Roger N. Beachy, Genetically Engineered Protection Against Viruses In Transgenic Plants, *Ann. Rev. Microbiol.* 47:739–63, (1993).
Indu. B. Maiti, John F. Murphy, John G. Shaw, and Arthur G. Hunt, Plant Biology, Plants that express a potyvirus proteinase gene are resistant to virus infection, *Proc. Natl. Acad. Sci. USA*, 90:6110–6114, (Jul. 1993).
The nucleotide sequences of the 3'–terminal regions of papaya ringspot virus strains W and P, Hector Quemada, Brigitte L'Hostis, Dennis Gonsalves, Ilene M. Reardon, Robert Heinrikson, Ernest L. Hiebert, Leang C. Sieu and Jerry L. Slightom, *Journal of General Virology*, 71:203–210, (1990).
P.F. Tennant, C. Gonsalves, K.–S. Ling, M. Fitch, R. Manshardt, J.L. Slightom, and D. Gonsalves, Differential Protection Against Papaya Ringspot Virus Isoltates in Coat Protein Gene Transgenic Papaya and Classically Cross–Protected Papaya, *The American Phytopathological Society*, 84:1359–1466 (1994).
S.–D. Yeh, D. Gonsalves, and R. Provvidenti, Comparative Studies on Host Range and Serology of Papaya Ringspot Virus and Watermelon Mosaic Virus 1, *The American Phytopathological Society*, 74:1081–1085 (1984).
Alexander R. van der Krol, Peter E. Lenting, Jetty Veenstra, Ingrid M. van der Meer, Ronald E. Koes, Anton G.M. Gerats, Joseph N.M. Mol & Antoine R. Stuitje, An anti––sense chalcone synthase gene in transgenic plants inhibits flower pigmentation, *Nature*, 333:866–869, (Jun. 30, 1988).

C.J.S. Smith, C.F. Watson, J.Ray, C.R. Bird, P.C. Moris, W. Schuch, & D. Grierson, Antisense RNA inhibition of polygalacturonase gene expression in transgenic tomatoes, *Nature*, 334 25:724–726 (Aug. 1988).
Structure and transcription of the nopaline synthase gene region of T–DNA, Michael Bevan, Wayne M. Barnes and Mary–Dell Chilton, *Nucleic Acids Research*, 11(2):369–385, (1983).
A. Depicker, S. Stachel, P.Dhaese, P. Zambryski, and H.M. Goodman, Nopaline Synthase: Transcript Mapping and DNA Sequence, *Journal of Molecular and Applied Genetics*, 1(6):561–573, (1982).
Jerzy Paszkowski, Raymond D. Shillito, Michael Saul, Vaclav Mandak, Thomas Hohn, Barbara Hohn and Ingo Potrykus, Direct gene transfer to plants, *The EMBO Journal*, vol. 3(12):2717–2722, (1984).
Anne Crossway, Janette V. Oakes, Jonathan M. Irvine, Barney Ward, Vic C Knauf, and C.K. Shewmaker, Integration of foreign DNA following microinjection of tobacco mesophyll protoplasts, *Mol. Gen. Genet.* 202:179–185, (1986).
Michael Fromm, Loverine P. Taylor, and Virginia Walbot, Expression of genes transferred into monocot and dicot plant cells by electroporation *Proc. Natl. Acad. Sci. USA*, 82:5824–5828, (Sep. 1985) Genetics.
T.M. Klein, E.D. Wolf, R. Wu & J. C. Sanford, High–velocity microprojectiles for delivering nucleic acids into living cells, *Nature*, 327 7:70–73, (May 1987).
D.E. Purcifull and E. Hiebert, Serological Distinction of Watermelon Mosaic Virus Isolates, *Phytopathology*, 69(2):112–116, (1979).
Indu B. Maiti, and Arthur G. Hunt, Crop Improvement via Biotechnology: An International Perspective, Expression of the Tobacco Vein Mottling Virus Nuclear Inclusion Protein (NIa) Gene In Tobacco, *J. Cell Biochem., Suppl. 16F*, 217 (1992).
S. Luis & R. Manshardt, Field Test of Virus Resistance In Transgenic Papayas, *91st Annual Meeting of the American Society for Horticultural Science Hortiscience*, 29:483 (1994).
Shigetou Namba, Kaishu Ling, Carol Gonsalves, Dennis Gonsalves and Jerry L. Stightom, Expression of the gene encoding the coat protein of cucumber mosaic virus (CMV) strain WL appears to provide protection to tobacco plants against infection by several different CMV strains, *Gene*, 107:181–188, (1991).
M. Bateson and J. Dale, The nucleotide sequence of the coat protein gene and 3' untranslated region of papaya ringspot virus type W (Aust), *Arch. Virol.* 123:101–109, (1992).
Marion F. Bateson, Juliane Henderson, Worawan Chaleeprom, Adrian J. Gibbs and James L. Dale, Papaya ringspot potyvirus: isolate variability and the origin of PRSV type P (Australia), *Journal of General Virology*, 75:3547–3553, (1994).
Yeh et al. Journal of General Virology. vol. 73, pp. 2531–2541, 1992.
Wang et al. Phytopathology. vol. 84, pp. 1205–1210, 1994.

*Primary Examiner*—James Ketter
*Assistant Examiner*—Irem Yucel
*Attorney, Agent, or Firm*—Rockey, Milnamow & Katz, Ltd.

[57] ABSTRACT

NIa protease genes of papaya ringspot virus strains FLA.83 W and USA P-type (HA attenuated) strain are provided.

34 Claims, 17 Drawing Sheets

Potyvirus Genome Map

FIG. 2a

```
                     Ncol                                                                EcoRI
                                           RMM354---> 5' GCTATGACAGAATTCACTGGCCTAA
                     CCATGGGCTTCTCTCTCC 1    CCATGGGCTTCTCTCTCCTTGGTATCATAAACACTATCCAGAGTAGATATTTAGTTGATCATTCAGTTGAGAATATCAGAAAGCTTCAACTAGCGAAGGC    100
       MetGlyPheSerLeuLeuGlyIleIleAsnThrIleGlnSerArgTyrLeuValAspHisSerValGluAsnIleArgLysLeuGlnLeuAlaLysAl
       M   G   F   S   L   L   G   I   I   N   T   I   Q   S   R   Y   L   V   D   H   S   V   E   N   I   R   K   L   Q   L   A   K   A 101  CCAGATTCAACAACTTGAAGCTCATGTGCAAGAGAACAATGTTGGAAATTTAATTCAATCTCTTGGTGCTGTTCGTCAGAGCTGTTTATCATCAAGGTGTTGAT    200
       aGlnIleGlnLeuGlnLeuGluAlaHisValGlnGluAsnAsnValGlyAsnLeuIleGlnSerLeuGlyAlaValArgAlaValTyrHisGlnGlyValAsp
       Q   I   Q   Q   L   E   A   H   V   Q   E   N   N   V   G   N   L   I   Q   S   L   G   A   V   R   A   V   Y   H   Q   G   V   D
                                                                                                                              C I       VPg 201  GGAGTCAAGCACATAAAGCGAGAGTTGGGCTTGAAAGGAGTTTGGGATGGTTCATTAATGATCAAGGATCGAATTGTATGCGGTTTCACAATGGCTGGTG    300
       GlyValLysHisIleLysArgGluLeuGlyLeuLysGlyValTrpAspGlySerLeuMetIleLysAspArgIleValCysGlyPheThrMetAlaGlyGly
       G   V   K   H   I   K   R   E   L   G   L   K   G   V   W   D   G   S   L   M   I   K   D   R   I   V   C   G   F   T   M   A   G   G 301  GTGCAATGCTCTTGTACCAACACTTTCGTGATAAGCTTACAAATGTACATGTGTTCACCAAGGTTTCTCTGCCGACAACGACAAAAGTTACGATTTAA    400
       lyAlaMetLeuLeuTyrGlnHisPheArgAspLysLeuThrAsnValHisValPheHisGlnGlyPheSerAlaArgGlnArgGlnLysLeuArgPheLy
       A   M   L   L   Y   Q   H   F   R   D   K   L   T   N   V   H   V   F   H   Q   G   F   S   A   R   Q   R   Q   K   L   R   F   K
                                                                                VPg|NIa 401  GTCAGCAGCAAATGCTAAGGTTGGTCGAGAAGTCTATGGAGATGACGGAGACATATTTCGGAGAAGCATACACAGAAAAGGAAACAAGAAG    500
       sSerAlaAlaAsnAlaLysValGlyArgGluValTyrGlyAspAspGlyThrIleGluHisTyrPheGlyGluAlaTyrThrLysLysGlyAsnLysLys
       S   A   A   N   A   K   L   G   R   E   V   Y   G   D   D   G   T   I   E   H   Y   F   G   E   A   Y   T   K   K   G   N   K   K 501  GGAAAGATGCATGGCATGGGTGTTAAAACGAGAAAGTTCGTTGCAACATATGGATTTAAACCAGAGGATTATTCATACGTGCGGTACTTGGATCCTTTAA    600
       GlyLysMetHisGlyMetGlyValLysThrArgLysPheValAlaThrTyrGlyPheLysProGluAspTyrSerTyrValArgTyrLeuAspProLeuT
       G   K   M   H   G   M   G   V   K   T   R   K   F   V   A   T   Y   G   F   K   P   E   D   Y   S   Y   V   R   Y   L   D   P   L   T 601  CAGGTGAGACTTTGGATGAAGCCCACAGACTGACATCTCAATGGTGCAAGAACATTTGGTGATATTCGGAGTAAATATTTGGATTGATCAGACAGCTTCGA    700
       hrGlyGluThrLeuAspGluAlaHisArgLeuThrSerGlnTrpCysLysAsnIleTrpAspIleArgSerLysTyrLeuAspSerAspSerPheAs
       G   E   T   L   D   E   S   P   Q   T   D   I   S   M   V   Q   E   H   F   G   D   I   R   S   K   Y   L   D   S   D   S   F   D
```

FIG. 2b

```
701  CAGGCAGGCTTTAATAGCAAACAATACAATTAAGGCCTATTATGTCCGAAGACAGCATTGGAAGTCGATTGACACCGCATAACCCTCTG          800
     pArgGlnAlaLeuIleAlaAsnAsnThrIleLysAlaTyrTyrValArgAsnSerAlaLysThrAlaLeuGluValAspLeuThrProHisAsnProLeu
        R  Q  A  L  I  A  N  N  T  I  K  A  Y  Y  V  R  N  S  A  K  T  A  L  E  V  D  L  T  P  H  N  P  L

801  AAAGTTTGTGACACAAATTGACTATTGCAGGATTTCCTGATAGAGAAGCTGAACTGAGACAAACAGGCCCAGAACTATTCAAGCCGATCAAGTTC         900
     LysValCysAspAsnLysLeuThrIleAlaGlyPheProAspArgGluAlaGluLeuArgGlnThrGlyProAlaArgThrIleGlnAlaAspGlnValP
        K  V  C  D  N  K  L  T  I  A  G  F  P  D  R  E  A  E  L  R  Q  T  G  P  A  R  T  I  Q  A  D  Q  V  P

901  CACCACCCTTCGAAATCAGTTCATCACGAAGGAAAAAGTCTTTGTCAAGGTATGAGAAATTACAATGGCATAGCTTCCGTGGTTTGCCATTTGAAAAACAC      1000
     roProProSerLysSerValHisHisGluGlyLysSerLeuCysGlnGlyMetArgAsnTyrAsnGlyIleAlaSerValValCysHisLeuLysAsnTh
        P  P  S  K  S  V  H  H  E  G  K  S  L  C  Q  G  M  R  N  Y  N  G  I  A  S  V  V  C  H  L  K  N  T

1001 ATCGGGAGATGGAGAAGCTATTTGGAATCGGATATAACTCGTTCATCATTACAAACCGACATTGTTCAAGAGAAATAATGGTGAACTTATAGTGAAA        1100
     rSerGlyAspGlyArgSerLeuPheGlyIleGlyTyrAsnSerPheIleIleThrAsnArgHisLeuPheLysGluAsnAsnGlyLeuLeuIleValLys
        S  G  D  G  R  S  L  F  G  I  G  Y  N  S  F  I  I  T  N  R  H  L  F  K  E  N  N  G  E  L  I  V  K

1101 TCCCAACACGGCAAGTTTGTGTCAAGAACACCTCAACGCTCCAGTTGGAAAAACTGATCTTTTGATAATTCGGATGCCGAAAGACTTTC             1200
     SerGlnHisGlyLysPheValValLysPheValValLysThrAspLeuLeuIleLeuIleIleArgMetProLysAspPheP
        S  Q  H  G  K  F  V  V  K  T  D  L  L  I  I  R  M  P  K  D  F  P

1201 CTCCATTCCATAGTAGCTAGGTTTAGGGCCATGAAAGCTGGAGACAAGGTTTGCATGATCGGTGTTGACTACCAAGAGAATCATATTGCGAGCAAAGT       1300
     roPheHisSerArgAlaArgPheArgAlaMetLysAlaGlyAspLysValCysMetIleGlyValAspTyrGlnGluAsnHisIleAlaSerLysVa
        P  F  H  S  R  A  R  F  R  A  M  K  A  G  D  K  V  C  M  I  G  V  D  Y  Q  E  N  H  I  A  S  K  V

1301 ATCTGAAACTTCTATTATCAGTGAGGGCACGGAGAGTTTGGATGCCGAAGATATCCACGAATGATGGTAATCCACTAGTTAGTGTTCA             1400
     lSerGluThrSerIleIleSerGluGlyThrGlyGluPheGlyCysHisTrpIleSerThrAsnAspGlyAspCysGlyAsnProLeuValSerValSer
        S  E  T  S  I  I  S  E  G  T  G  E  F  G  C  H  W  I  S  T  N  D  G  D  C  G  N  P  L  V  S  V  S

1401 GATGGTTTCATTGTTGGCTTGCATAGTTTGTCGACATCAACCGGAAATCAAATTTCTTCGCTAAAATACCCGCACATTTGAAGAAAAGGTCCTGAGGA       1500
     AspGlyPheIleValGlyLeuHisSerLeuSerThrSerThrGlyAsnGlnAsnPhePheAlaLysIleProAlaGlnPheGluGluLysValLeuArgL
        D  G  F  I  V  G  L  H  S  L  S  T  S  T  G  N  Q  N  F  F  A  K  I  P  A  Q  F  E  E  K  V  L  R  K
```

FIG. 2c

```
1501 AAATTGATGAATTAACATGGAGCAAACACTGAGCTACAATATTAATGAACTGAGTGGGAGCTCTTAAGGTGTGGGAAAGTCGTCCCGAAGCAATTT  1600
     ysIleAspGluLeuThrTrpSerLysHisTrpSerTyrAsnIleAsnGluLeuSerTrpGluAlaLeuLysValTrpGluSerArgProGluAlaIlePh
      I  D  E  L  T  W  S  K  H  W  S  Y  N  I  N  E  L  S  W  G  A  L  K  V  W  E  S  R  P  E  A  I  F

1601 TAATGCGCAAAAGGAAGTCAACCAATTGAATGTTTTGAGCAAAGTGGTAGTCGTTGGCTCGTTCGACAAATTACACGGCAATTTGAAGGGTGTAAGTTCC  1700
     eAsnAlaGlnLysGluValAsnGlnLeuAsnValPheGluGlnSerGlySerArgTrpLeuPheAspLysLeuHisGlyAsnLeuLysGlyValSerSer
      N  A  Q  K  E  V  N  Q  L  N  V  F  E  Q  S  G  S  R  W  L  F  D  K  L  H  G  N  L  K  G  V  S  S
                                              NIa|NIb
                                                                                 NcoI       BamHI
                                            RMM355 <--- 3' CACACTACTTATCCGGTACCAAAGAACCTAGGTGAATACCC

1701 GCTTCTAGCAATTTGGTGACAAAGCACGTTGTTAAAGGCATTTGTCCTCTCTTCAGGAACTATCTCGAGTGTGATGAATAGGCCCATGG 1789
     AlaSerSerAsnLeuValThrLysHisValValLysGlyIleCysProLeuPheArgAsnTyrLeuGluCysAspGluEndAlaHis
      A  S  S  N  L  V  T  K  H  V  V  K  G  I  C  P  L  F  R  N  Y  L  E  C  D  E  *  A  H
```

FIG. 3a

```
                    20C
101
HA-P    GCACTGGCCT AAACTCTAGC TTCTCTCTCC TTGGTGTTAT AAACACTATC CAGAGTAGAT ATCTAGTTGA CCACTCAGTT GAAAATATCA GAAAACTTCA
USA-P   GCACTGGCCT AAACTCTAGC TTCTCTCTCC TTGGTGTTAT AAACACTATC CAGAGTAGAT ATCTAGTTGA CCACTCAGTT GAAAATATCA GAAAACTTCA
Fla83-W ..........  ..CCATGGGC TTCTCTCTCC TTGGTATCAT AAACACTATC CAGAGTAGAT ATTTAGTTGA TCATTCAGTT GAGAATATCA GAAAGCTTCA
                                                                                                           300
201
HA-P    ACTGGCAAAG GCCCAGATTC AACAACTTGA AGCTCACATG CAGGAAAACA ATGTTGAAAA TTTAATTCAA TCTCTTGGTG TCTCTTGGTG CTGTAAGAGC TGTTTACCAT
USA-P   ACTGGGCAAG GCCCAAATTC AACAACTTGA AGCTCATGTG CAGGAAAACA ATGTTGAAAA TTTAATTCAA TCTCTTGGTG TCTCTTGGTG CTGTCAGAGC TGTTTACCAT
Fla83-W ACTAGCGAAG GCCCAGATTC AACAACTTGA AGCTCATGTG CAAGAGAACA ATGTTGGAAA TTTAATTCAA TCTCTTGGTG TCTCTTGGTG CTGTCAGAGC TGTTTATCAT
                                                                                                           400
301
HA-P    CAAAGTGTTG ATGGATTTAA ACACATAAAG CGAGAGTTGG GTTTGAAAGG AGTTTGGGAT GGCTCATTGA TGATTAAGGA TGCGATTGTA TGCGGTTTCA
USA-P   CAAAGTGTTG ATGGATTTAA ACACATAAAG CGAGAGTTGG GTTTGAAAGG AGTTTGGGAT GGCTCATTGA TGATTAAGGA TGCGATTGTA TGCGGTTTCA
Fla83-W CAAGGTGTTG ATGGAGTCAA GCACATAAAG CGAGAGTTGG GCTTGAAAGG AGTTTGGGAT GGTTCATTAA TGATCAAGGA TCGAATTGTA TGCGGTTTCA
                                                                                                           500
401
HA-P    CAATGGCTGG CGGTGCGATG CTTTTGTACC AACACTTTCG TGATAAGTTT ACAAATGTTC ATGTGTTTCA CCAAGGTTTC TCTGCCGCGAC AGAGACAAAA
USA-P   CAATGGCTGG CGGTGCGATG CTTTTGTACC AACATTTTCG TGATAAGTTT ACAAATGTTC ATGTGTTTCA CCAAGGTTTC TCTGCCGCGAC AGAGACAAAA
Fla83-W CAATGGCTGG TGGTGCAATG CTCTTGTACC AACACTTTCG TGATAAGCTT ACAAATGTAC ATGTGTTTCA CCAAGGTTTC TCTGCCGCGAC AACGACAAAA
                                                                                                           600
501
HA-P    GTTAAGATTT AAGTCAGCAG CGAATGCTAA GCTTGGTCGA GAGGTCTATG GAGATGATGG GACAATTGAG CACTATTTTG GAGAAGCGTA CACGAAGAAA
USA-P   GTTAAGATTT AAGTCAGCAG CGAATGCTAA GCTTGGTCGA GAGGTCTATG GAGATGATGG GACAATTGAG CACTATTTTG GAGAAGCGTA CACGAAGAAA
Fla83-W GTTACGATTT AAGTCAGCAG CAAATGCTAA GCTTGGTCGA GAAGTCTATG GAGATGACGG GACAATTGAG CACTATTTCG GAGAAGCATA CACAAAGAAA
                                                                                                           700
601
HA-P    GGAAACAAGA AAGGAAAGAT GCATGGCATG GGTGTTAAGA CGAGAAAGTT TGTTGCGACA TATGGATTTA AACCGGAGGA TTACTCGTAC GTGCGGTACT
USA-P   GGAAACAAGA AAGGAAAGAT GCATGGCATG GGTGTTAAGA CGAGAAAGTT TGTTGCGACA TATGGATTTA AACCGGAGGA TTACTCGTAC GTGCGGTACT
Fla83-W GGAAACAAGA AGGGAAAGAT GCATGGCATG GGTGTTAAAA CGAGAAAGTT CGTTGCAACA TATGGATTTA AACCAGAGGA TTATTCATAC GTGCGGTACT
                                                                                                           800
701
HA-P    TGGACCCTTT AACAGGTGAG ACTTTGGATG AAAGCCCACA GACTGATATC TCAATGGTGC AAGATCATTT TAGTGATATT CGGAGAAAGT ACATGGATTC
USA-P   TGGACCCTTT AACAGGTGAG ACTTTGGATG AAAGCCCACA GACTGATATC TCAATGGTGC AAGATCATTT TAGTGATATT CGGAGAAAGT ACATGGATTC
Fla83-W TGGATCCTTT AACAGGTGAG ACTTTGGATG AAAGCCCACA GACTGACATC TCAATGGTGC AAGAACATTT TGGTGATATT CGGAGTAAAT ATTTGGATTC
```

FIG. 3b

```
        801
HA-P    AGACAGCTTC GATAGGCAGG CTTTAATAGC AAACAATACA ATTAAGGCTT ATTATGTCCG AAACTCCGCG AAGGCAGCAT TGGAAGTCGA TCTGACACCG
USA-P   AGACAGCTTC GATAGGCAGG CTTTAATAGC AAACAATACA ATTAAGGCTT ATTATGTCCG AAACTCCGCG AAGGCAGCAT TGGAAGTCGA TCTGACACCG
Fla83-W AGACAGCTTC GACAGGCAGG CTTTAATAGC AAACAATACA ATTAAGGCCT ATTATGTCCG AAACTCCGCG AAGACAGCAT TGGAAGTCGA TTTGACACCG
                                                                                                                900

901
HA-P    CACAACCCTC TCAAAGTTTG TGACAATAAA TTGACCATTG CAGGATTTCC TGACAGGGAA GCTGAGCTAA GACAAACAGG CCCGCCCAGA ACTATTCAAG
USA-P   CACAACCCTC TCAAAGTTTG TGACAATAAA TTGACCATTG CAGGATTTCC TGACAGGGAA GCTGAGCTGA GACAAACAGG CCCGCCCAGA ACTATTCAAG
Fla83-W CATAACCCTC TGAAAGTTTG TGACAACAAA TTGACTATTG CAGGATTTCC TGATAGAGAA GCTGAACTGA GACAAACAGG CCCAGCCAGA ACTATTCAAG
                                                                                                               1000

1001
HA-P    TAGATCAAGT GCCACCACCC TCGAAATCAG TTCATCACGA AGGAAAAAGT CTTTGTCAAG GCATGAGAAA TTACAATGGC ATAGCTTCTG TGGTTTGCCA
USA-P   TAGATCAAGT GCCACCACCC TCGAAATCAG TTCATCACGA AGGAAAAAGT CTTTGTCAAG GCATGAGAAA TTACAATGGC ATAGCTTCTG TGGTTTGCCA
Fla83-W CCGATCAAGT TCCACCACCT TCGAAATCAG TTCATCACGA AGGAAAAAGT CTTTGTCAAG GTATGAGAAA TTACAATGGC ATAGCTTCCG TGGTTTGCCA
                                                                                                               1100

1101
HA-P    TTTGAAAAAC ACATCAGGAA AGGGGAAGAG CTTGTTTGGA ATTGTCAAGA ACACCACACA ACTCCAAATT GCTCCAGTTG GAAAGACTGA TCTTTTAATT ATTCGGATGC
USA-P   TTTGAAAAAC ACATCAGGAA AGGGGAAAGA CTTGTTTGGA ATTGTCAAGA ACACCACACA ACTCCCGAATT GCTCCAGTTG GAAAGACTGA TCTTTTAATT ATTCGGATGC
Fla83-W TTTGAAAAAC ACATCGGGAG ATGGGAGAAG CCTATTTGGA GTTGTCAAGA ACACCTCAAC ACTCGTTCAT GCTCCAGTTG GAAAAACTGA TCTTTGATA ATTCGGATGC
                                                                                                                       1200

1201
HA-P    CTTATAGTGA AATCCCAACA CGGTAAGTTT ATTGTCAAGA GGCCATGAAA GCTGGGGACA AGGTTTGCAT GATAGGTGTT GACTACCAAG AGAATCATAT
USA-P   CTTATAGTGA AATCCCAACA CGGTAAGTTT ATTGTCAAGA GGCCATGAAA GCTGGGGACA AGGTTTGCAT GATAGGTGTT GACTACCAAG AGAATCATAT
Fla83-W CTTATAGTGA AATCCCAACA CGGCAAGTTT GTTGTCAAGA GGCCATGAAA GCTGGAGACA AGGTTTGCAT GATCGGTGTT GACTACCAAG AGAATCATAT
                                                                                                               1300

1301
HA-P    CGAAAGATTT TCCTCCATTC CATAGCAGAG CCTCTATCAT CAGTGAGGGC ACGGGAGATT TTGGATGCCA CTGGATATCC ACGAATGACG GTGATTGCGG
USA-P   CGAAAGATTT TCCTCCATTC CATAGCAGAG CCTCTATCAT CAGTGAGGGC ACGGGAGATT TTGGATGCCA CTGGATATCC ACGAATGACG GTGATTGCGG
Fla83-W CGAAAGACTT TCCTCCATTC CATAGTAGAG CTTCTATTAT CAGTGAGGGC ACGGGAGAGT TTGGATGCCA TTGGATATCC ACGAATGATG GTGATTGCGG
                                                                                                               1400

1401
HA-P    CGGAGCAAAA GTATCTGAAA CCTCTATCAT CAGTGAGGGC ACGGGAGATT TTGGATGCCA CTGGATATCC ACGAATGACG GTGATTGCGG TAATCCTTTA
USA-P   CGGAGCAAAA GTATCTGAAA CCCTCTATCAT CAGTGAGGGC ACGGGAGATT TTGGATGCCA CTGGATATCC ACGAATGACG GTGATTGCGG TAATCCTTTA
Fla83-W TGCGAGCAAA GTATCTGAAA CTTCTATTAT CAGTGAGGGC ACGGGAGAGT TTGGATGCCA TTGGATATCC ACGAATGATG GTGATTGCGG TAATCCACTA
                                                                                                               1500
```

FIG. 3c

```
       1501                                                                                    1600
HA-P   GTTAGTGTTT CAGATGGTTT TATTGTCGGC TTGCATAGTT TGTCGACATC AACTGGAGAT CAAAATTTCT TTGCCAAAAT ACCCGCACAA TTTGAAGAAA
USA-P  GTTAGTGTTT CAGATGGTTT TATTGTCGGC TTGCATAGTT TGTCGACATC AACTGGAGAT CAAAATTTCT TTGCTAAAAT ACCCGCACAA TTTGAAGAAA
Fla83-W GTTAGTGTTT CAGATGGTTT CATTGTTGGC TTGCATAGTT TGTCGACATC AACCGGAAAT CAAAATTTCT TCGCTAAAAT ACCCGCACAA TTTGAAGAAA 1601                                                                                    1700
HA-P   AGGTCCTTAG GAAGATTGAT GATTTAACTT GGAGCAAACA CTGGAGCTAT AATATTAATG AACTGAGTTG GGGAGCTCTC AAAGTGTGGG AAAGTCGGCC
USA-P  AGGTCCTTAG GAAGATTGAT GATTTAACTT GGAGCAAACA CTGGAGCTAT AATATTAATG AACTGAGTTG GGGAGCTCTC AAAGTGTGGG AAAGTCGGCC
Fla83-W AGGTCCTGAG GAAAATTGAT GAATTAACAT GGAGCAAACA CTGGAGCTAC AATATTAATG AACTGAGTTG GGGAGCTCTT AAGGTGTGGG AAAGTCGTCC 1701                                                                                    1800
HA-P   CGAAGCAATT TTTAACGCAC AAAAGGAAGT TAATCAATTG AATGTTTTCG AGCAAAGTGG TGGTCGTTGG CTCTTTGACA AATTACACGG CAATTTGAAA
USA-P  CGAAGCAATT TTTAACGCGC AAAAGGAAGT TAATCAATTG AATGTTTTCG AGCAAAGTGG TAGTCGTTGG CTCTTTGACA AATTACACGG CAATTTGAAA
Fla83-W CGAAGCAATT TTTAATGCGC AAAAGGAAGT CAACCAATTG AATGTTTTTG AGCAAAGTGG TAGTCGTTGG CTCTTCGACA AATTACACGG CAATTTGAAG 1801                                                                                    1900
HA-P   GGAGTTAGCT CCGCTCCTAG CAATTTGGTG ACAAAGCACG TTGTTAAAGG AATTTGTCCT CTTTTCAGGA ACTATCTCGA GTGTGATGAA GAGGCTAAAG
USA-P  GGAGTTAGCT CCGCTCCTAG CAATTTGGTG ACAAAGCACG TTGTTAAAGG AATTTGTCCT CTTTTCAGGA ACTATCTCGA GTGTGATGAA GAGGCTAAAG
Fla83-W GGTGTAAGTT CCGCTTCTAG CAATTTGGTG ACAAAGCACG CATTTGTCCT CTCTTCAGGA ACTATCTCGA GTGTGATGAA TAGGCCCATG 1901                                                                                    2000
HA-P   CTTTCTTTAG TCCACTTATG GGTCACTACA TGAAGAGTGT TCTGAGCAAG GAAGCGTACA TTAAGGATTT ATTGAAATAT TCAAGTGATA TTGTCGTTGG
USA-P  CTTTCTTTAG TCCACTTATG GGTCACTACA TGAAGAGTGT TCTGAGCAAG GAAGCGTACA TTAAGGATTT ATTGAAATAT TCAAGTGATA TTGTCGTTGG
Fla83-W G
```

FIG. 4a

```
                                                                                                    Q/G
                                                                                                    CI/VPg
                                                                                                      *
  1                                                                                                        100
Fla83-W ............ ............ ............ ....MGFSLL GINTIQSRY  LVDHSVENIR KLQLAKAQIQ QLEAHVQENN VGNLIQSLGA VRAVYHQGVD GVKHIKRELG
USA-P   ............ ............ ............ ....SSFSLL GVINTIQSRY LVDHSVENIR KLQLAKAQIQ QLEAHVQENN VENLIQSLGA VRAVYHQSVD GFKHIKRELG
HA-P    ............ ............ ............ ....SSFSLL GVINTIQSRY LVDHSVENIR KLQLAKAQIQ QLEAHMQENN VENLIQSLGA VRAVYHQSVD GFKHIKRELG
                                                      1                                          2                          3
                                               Q/G
                                               VPg/NIa
                                                       *                                  *
 101                                                                                                       200
Fla83-W LKGVWDGSLM IKDRIVCGFT MAGGAMLLYQ HFRDKLTNVH VFHQGFSARQ RQKLRFKSAA NAKLGREVYG DDGTIEHYFG EAYTKKGNKK GKMHGMGVKT
USA-P   LKGVWDGSLM IKDAIVCGFT MAGGAMLLYQ HFRDKFTNVH VFHQGFSARQ RQKLRFKSAA NAKLGREVYG DDGTIEHYFG EAYTKKGNKK GKMHGMGVKT
HA-P    LKGVWDGSLM IKDAIVCGFT MAGGAMLLYQ HFRDKFTNVH VFHQGFSARQ RQKLRFKSAA NAKLGREVYG DDGTIEHYFG EAYTKKGNKK GKMHGMGVKT
                       4              5

201                 *             *                                            *                         300
Fla83-W RKFVATYGFK PEDYSYVRYL DPLTGETLDE SPQTDISMVQ EHFGDIRSKY LDSDSFDRQA LIANNTIKAY YVRNSAKTAL EVDLTPHNPL KVCDNKLTIA
USA-P   RKFVATYGFK PEDYSYVRYL DPLTGETLDE SPQTDISMVQ DHFSDIRRKY MDSDSFDRQA LIANNTIKAY YVRNSAKAAL EVDLTPHNPL KVCDNKLTIA
HA-P    RKFVATYGFK PEDYSYVRYL DPLTGETLDE SPQTDISMVQ DHFSDIRRKY MDSDSFDRQA LIANNTIKAY YVRNSAKAAL EVDLTPHNPL KVCDNKLTIA
                                                         6         7          8                       9

301                *                                                                 *                   *400
Fla83-W GFPDREAELR QTGPARTIQA DQVPPPSKSV HHEGKSLCQG MRNYNGIASV VCHLKNTSGD GRSLFGIGYN SFIITNRHLF KENNGELIVK SQHGKFVKN
USA-P   GFPDREAELR QTGPPRTIQV DQVPPPSKSV HHEGKSLCQG MRNYNGIASV VCHLKNTSGK GKSLFGIGYN SFIITNRHLF KENNGELIVK SQHGKFIVKN
HA-P    GFPDREAELR QTGPPRTIQV DQVPPPSKSV HHEGKSLCQG MRNYNGIASV VCHLKNTSGK GKSLFGIGYN SFIITNRHLF KENNGELIVK SQHGKFIVKN
                  10         11                                        12                                         13

*   *                                                             *
                                                                                                          500
Fla83-W TSTLRIAPVG KTDLLIIRMP KDFPPFHSRA RFRAMKAGDK VCMIGVDYQE NHIASKVSET SIISEGTGEF GCHWISTNDG DCGNPLVSVS DGFIVGLHSL
USA-P   TTTLRIAPVG KTDLLIIRMP KDFPPFHSRA RFRAMKAGDK VCMIGVDYQE NHIASKVSET SIISEGTGDF GCHWISTNDG DCGNPLVSVS DGFIVGLHSL
HA-P    TTTLQIAPVG KTDLLIIRMP KDFPPFHSRA RFRAMKAGDK VCMIGVDYQE NHIASKVSET SIISEGTGDF GCHWISTNDG DCGNPLVSVS DGFIVGLHSL
           14                                                                                   15
```

FIG. 4b

```
                                                                                       Q/S
        501  *                      *                                                 NIa/NIb                                 600
Fla83-W STSTGNQNFF AKIPAQFEEK VLRKIDELTW SKHWSYNINE LSWGALKVWE SRPEAIFNAQ KEVNQLNVFE QSGSRWLFDK LHGNLKGVSS ASSNLVTKHV
  USA-P STSTGDQNFF AKIPAQFEEK VLRKIDDLTW SKHWSYNINE LSWGALKVWE SRPEAIFNAQ KEVNQLNVFE QSGSRWLFDK LHGNLKGVSS APSNLVTKHV
   HA-P STSTGDQNFF AKIPAQFEEK VLRKIDDLTW SKHWSYNINE LSWGALKVWE SRPEAIFNAQ KEVNQLNVFE QSGGRWLFDK LHGNLKGVSS APSNLVTKHV
            16                     17

601
Fla83-W VKGICPLFRN YLECDE*AH.
  USA-P VKGICPLFRN YLECDEEAKA
   HA-P VKGICPLFRN YLECDEEAKA
```

```
601  CAGGTGAGACTTTGGATGATGAAAGCCCACAGACTGATATCTCAATGGTGCAAGATCATTTAGTGATATTCGGAGAAAGTACATGGATTCAGACAGCTTCGA      700
     hrGlyGluThrLeuAspGluSerProGlnThrAspIleSerMetValGlnAspIleSerMetValGlnAspHisPheSerAspIleArgArgLysTyrMetAspSerAspSerPheAs
     G  E  T  L  D  E  S  P  Q  T  D  I  S  M  V  Q  D  H  F  S  D  I  R  R  K  Y  M  D  S  D  S  F  D

701  TAGGCAGGCTTTAATAGCAAACAATACAATTAAGGCTTATTATGTCCGAAAACTCCGGCGAAGTCGATCTGACACCGCACAACCCTCTC      800
     pArgGlnAlaLeuIleAlaAsnAsnThrIleLysAlaTyrTyrValArgAsnSerAlaAlaLeuGluValAspLeuThrProHisAsnProLeu
     R  Q  A  L  I  A  N  N  T  I  K  A  Y  Y  V  R  N  S  A  K  A  A  L  E  V  D  L  T  P  H  N  P  L

801  AAAGTTTGTGACAATAAATTGACCATTGCAGGATTTCCTGACAGGGAAGCTGAGCTGAGACAAACAGGCCCCGCCAAGAACTATTCAAGTAGATCAAGTGC      900
     LysValCysAspAsnLysLeuThrIleAlaGlyPheProAspArgArgGluAlaGluLeuArgGlnThrGlyProProArgThrIleGlnValAspGlnValP
     K  V  C  D  N  K  L  T  I  A  G  F  P  D  R  R  E  A  E  L  R  Q  T  G  P  P  R  T  I  Q  V  D  Q  V  P

901  CACCACCCTCGAAATCAGTTCATCACGAAGGAAAAAGTCTTTGTCAAGGCATGAGAAATTACAATGGCATAGCTTCTGTGGTTTGCCATTGAAAAACAC      1000
     roProProSerLysSerValHisHisGluGlyLysLeuCysGlyGlnGlyMetArgAsnTyrAsnGlyIleAlaSerValValCysHisLeuLysAsnTh
     P  P  S  K  S  V  H  H  E  G  K  S  L  C  Q  G  M  R  N  Y  N  G  I  A  S  V  V  C  H  L  K  N  T

1001 ATCAGGAAAGGGAAAGAGCTTGTTTGGAATTGGAATATAATTCATTCATTCAAGGAGAATAATGGAACTTATTGTTCAAGGAGAATAATGTGAACTTATAGTGAAA      1100
     rSerGlyLysGlyLysSerLeuPheGlyIleGlyTyrAsnSerPheIleIleThrAsnArgHisLeuPheLysGluAsnAsnGlyLeuGluLeuIleValLys
     S  G  K  G  K  S  L  F  G  I  G  Y  N  S  F  I  I  T  N  R  H  L  F  K  E  N  N  G  E  L  I  V  K

1101 TCCCAACACGGTAAGTTTATTGTCAAGAACACCACAACTCCAGTTGAAAGACTGATCTTTAATTATTCGGATGCCGAAAGATTTTC      1200
     SerGlnHisGlyLysPheIleValLysAsnThrThrThrLeuArgIleAlaProValGlyLysThrAspLeuLeuIleIleArgMetProLysAspPheP
     S  Q  H  G  K  F  I  V  K  N  T  T  T  L  R  I  A  P  V  G  K  T  D  L  L  I  I  R  M  P  K  D  F  P

1201 CTCCATTCCATAGCAGAGCTAGGTTTAGGGCCATGAAAGCTGGGACAAGGTTTGACATGATAGGTGTTGACTAGGTGTTGACTACCAAGAGAATCATATCGCAGCAAGT      1300
     roPheHisSerArgAlaArgPheArgAlaMetLysAlaGlyAspLysValCysMetIleGlyValAspTyrGlnGluAsnHisIleAlaSerLysVa
     P  F  H  S  R  A  R  F  R  A  M  K  A  G  D  K  V  C  M  I  G  V  D  Y  Q  E  N  H  I  A  S  K  V

1301 ATCTGAAACCTCTATCATCAGTGAGGGCACGGGAGATTTGGATGCCACTGGATATCCACGAATGACGGTGATTGCGTAATCCTTTAGTAGTGTTTCA      1400
     lSerGluThrSerIleIleSerGluGluGlyThrGlyTyrAspPheGlyCysHisTrpIleSerThrAsnAspGlyAspCysGlyAsnProLeuValSerValSer
     S  E  T  S  I  I  S  E  G  T  G  D  F  G  C  H  W  I  S  T  N  D  G  D  C  G  N  P  L  V  S  V  S
```

FIG. 5c

```
1401 GATGGTTTATTGTCGGCTTGCATAGTTTGTCGACATCAACTGGAGATCAACTGGAGATCAAAATTCTTTGCTAAAATACCCGCACAATTTGAAGAAAAGGTCCTTAGGA      1500
     AspGlyPheIleValGlyLeuHisSerLeuHisSerLeuSerThrSerGlyAspGlnAsnPhePheAlaAlaLysIleProAlaGlnPheGluGluLysValLeuArgL
      D  G  F  I  V  G  L  H  S  L  S  T  S  T  G  D  Q  N  F  F  A  K  I  P  A  Q  F  E  E  K  V  L  R  K

1501 AGATTGATGATTAACTTGGAGCAAACACTGGAGCTATAATATTAATGAACTGAGTGGGAGCTCTCAAAGTGTGGGAAAGTCGGCCCGAAGCAATTT                1600
     ysIleAspAspLeuThrTrpSerLysHisTrpSerTyrAsnIleAsnGluLeuSerTrpGlyAlaLeuLysValTrpGluSerArgProGluAlaIlePh
      I  D  D  L  T  W  S  K  H  W  S  Y  N  I  N  E  L  S  W  G  A  L  K  V  W  E  S  R  P  E  A  I  F
                                                        NcoI  BamHI
                                          RMM334 <--- 3' AAGCTCGTTGATCCAGATGGGTACCCTAGGCTGTTTAAT

1601 TAACGCGGCAAAAGGAAGTTAATCAATTGAATGTTTTCGAGCAAAGTGGTAGTCGTTGGCTCTTTGACAAATTACACGGCAATTTGAAAGGAGTTAGCTCC          1700
     eAsnAlaGlnLysGluValAsnGlnLeuAsnValPheGluGlnSerGlySerArgTrpLeuPheAspLysPheLeuHisGlyAsnLeuLysGlyValSerSer
      N  A  Q  K  E  V  N  Q  L  N  V  F  E  Q  S  G  S  R  W  L  F  D  K  L  H  G  N  L  K  G  V  S  S
                                     NIa|NIb                               NcoI    BamHI
                                                       RMM355 <--- 3' CACACTACTTATCCGGGTACCAAAGAACCTAGGTGAATACCC

1701 GCTCCTAGCAATTGGTGACAAAGCACGTTGTTAAAGGAATTTGTCCTCTTTCAGGAACTATCTCGAGTGTGATGAAtAGGCCCATGGTTGCGCTG        1797
     AlaProSerAsnLeuValThrLysHisValValLysGlyIleCysProLeuPheArgAsnTyrLeuGlyIleCysAspGluEndAlaHisGlyCysAla
      A  P  S  N  L  V  T  K  H  V  V  K  G  I  C  P  L  F  R  N  Y  L  E  C  D  E  *  A  H  G  C  A
```

Insert PRV NIa-1(stop)(HA) cpexpress partial HindIII fragments into pUC1318 pUC1318 — BP#1, HindIII, BamHI, XbaI, EcoRI cpexpress NIa-1(stop)(HA) — BP#1, HindIII, BamHI, HindIII, EcoRI, BamHI, HindIII, SstI Isolate BamHI cpexpress fragments BamHI — HindIII — SstI — BamHI PRVNIa-1(stop)(HA)

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1789 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: PAPAYA RINGSPOT VIRUS (B) STRAIN: W-TYPE
(C) INDIVIDUAL ISOLATE: Florida 83

(ix) FEATURE:
(A) NAME/KEY: CDS
(B) LOCATION: 3..1783

(ix) FEATURE:
(A) NAME/KEY: mat_peptide
(B) LOCATION: 3..191

(ix) FEATURE:
(A) NAME/KEY: mat_peptide
(B) LOCATION: 192..362

(ix) FEATURE:
(A) NAME/KEY: mat_peptide
(B) LOCATION: 363..1643

(ix) FEATURE:
(A) NAME/KEY: mat_peptide
(B) LOCATION: 1644..1783

(xi) SEQUENCE DESCRIPTION: SEQ ID NO:1:

```
CC  ATG  GGC  TTC  TCT  CTC  CTT  GGT  ATC  ATA  AAC  ACT  ATC  CAG  AGT  AGA        47
    Met  Gly  Phe  Ser  Leu  Leu  Gly  Ile  Ile  Asn  Thr  Ile  Gln  Ser  Arg
    1              5                        10                       15

TAT  TTA  GTT  GAT  CAT  TCA  GTT  GAG  AAT  ATC  AGA  AAG  CTT  CAA  CTA  GCG        95
Tyr  Leu  Val  Asp  His  Ser  Val  Glu  Asn  Ile  Arg  Lys  Leu  Gln  Leu  Ala
                    20                       25                       30

AAG  GCC  CAG  ATT  CAA  CAA  CTT  GAA  GCT  CAT  GTG  CAA  GAG  AAC  AAT  GTT       143
Lys  Ala  Gln  Ile  Gln  Gln  Leu  Glu  Ala  His  Val  Gln  Glu  Asn  Asn  Val
               35                       40                       45

GGA  AAT  TTA  ATT  CAA  TCT  CTT  GGT  GCT  GTC  AGA  GCT  GTT  TAT  CAT  CAA       191
Gly  Asn  Leu  Ile  Gln  Ser  Leu  Gly  Ala  Val  Arg  Ala  Val  Tyr  His  Gln
          50                       55                       60

GGT  GTT  GAT  GGA  GTC  AAG  CAC  ATA  AAG  CGA  GAG  TTG  GGC  TTG  AAA  GGA       239
Gly  Val  Asp  Gly  Val  Lys  His  Ile  Lys  Arg  Glu  Leu  Gly  Leu  Lys  Gly
     65                       70                       75

GTT  TGG  GAT  GGT  TCA  TTA  ATG  ATC  AAG  GAT  CGA  ATT  GTA  TGC  GGT  TTC       287
Val  Trp  Asp  Gly  Ser  Leu  Met  Ile  Lys  Asp  Arg  Ile  Val  Cys  Gly  Phe
80                       85                       90                       95

ACA  ATG  GCT  GGT  GGT  GCA  ATG  CTC  TTG  TAC  CAA  CAC  TTT  CGT  GAT  AAG       335
Thr  Met  Ala  Gly  Gly  Ala  Met  Leu  Leu  Tyr  Gln  His  Phe  Arg  Asp  Lys
                    100                      105                      110

CTT  ACA  AAT  GTA  CAT  GTG  TTT  CAC  CAA  GGT  TTC  TCT  GCG  CGA  CAA  CGA       383
Leu  Thr  Asn  Val  His  Val  Phe  His  Gln  Gly  Phe  Ser  Ala  Arg  Gln  Arg
               115                      120                      125

CAA  AAG  TTA  CGA  TTT  AAG  TCA  GCA  GCA  AAT  GCT  AAG  CTT  GGT  CGA  GAA       431
Gln  Lys  Leu  Arg  Phe  Lys  Ser  Ala  Ala  Asn  Ala  Lys  Leu  Gly  Arg  Glu
          130                      135                      140

GTC  TAT  GGA  GAT  GAC  GGG  ACA  ATT  GAG  CAC  TAT  TTC  GGA  GAA  GCA  TAC       479
Val  Tyr  Gly  Asp  Asp  Gly  Thr  Ile  Glu  His  Tyr  Phe  Gly  Glu  Ala  Tyr
     145                      150                      155

ACA  AAG  AAA  GGA  AAC  AAG  AAG  GGA  AAG  ATG  CAT  GGC  ATG  GGT  GTT  AAA       527
Thr  Lys  Lys  Gly  Asn  Lys  Lys  Gly  Lys  Met  His  Gly  Met  Gly  Val  Lys
160                      165                      170                      175

ACG  AGA  AAG  TTC  GTT  GCA  ACA  TAT  GGA  TTT  AAA  CCA  GAG  GAT  TAT  TCA       575
Thr  Arg  Lys  Phe  Val  Ala  Thr  Tyr  Gly  Phe  Lys  Pro  Glu  Asp  Tyr  Ser
                    180                      185                      190

TAC  GTG  CGG  TAC  TTG  GAT  CCT  TTA  ACA  GGT  GAG  ACT  TTG  GAT  GAA  AGC       623
Tyr  Val  Arg  Tyr  Leu  Asp  Pro  Leu  Thr  Gly  Glu  Thr  Leu  Asp  Glu  Ser
               195                      200                      205

CCA  CAG  ACT  GAC  ATC  TCA  ATG  GTG  CAA  GAA  CAT  TTT  GGT  GAT  ATT  CGG       671
Pro  Gln  Thr  Asp  Ile  Ser  Met  Val  Gln  Glu  His  Phe  Gly  Asp  Ile  Arg
          210                      215                      220
```

```
AGT  AAA  TAT  TTG  GAT  TCA  GAC  AGC  TTC  GAC  AGG  CAG  GCT  TTA  ATA  GCA    719
Ser  Lys  Tyr  Leu  Asp  Ser  Asp  Ser  Phe  Asp  Arg  Gln  Ala  Leu  Ile  Ala
     225                      230                      235

AAC  AAT  ACA  ATT  AAG  GCC  TAT  TAT  GTC  CGA  AAC  TCC  GCG  AAG  ACA  GCA    767
Asn  Asn  Thr  Ile  Lys  Ala  Tyr  Tyr  Val  Arg  Asn  Ser  Ala  Lys  Thr  Ala
240                      245                      250                      255

TTG  GAA  GTC  GAT  TTG  ACA  CCG  CAT  AAC  CCT  CTG  AAA  GTT  TGT  GAC  AAC    815
Leu  Glu  Val  Asp  Leu  Thr  Pro  His  Asn  Pro  Leu  Lys  Val  Cys  Asp  Asn
                    260                      265                      270

AAA  TTG  ACT  ATT  GCA  GGA  TTT  CCT  GAT  AGA  GAA  GCT  GAA  CTG  AGA  CAA    863
Lys  Leu  Thr  Ile  Ala  Gly  Phe  Pro  Asp  Arg  Glu  Ala  Glu  Leu  Arg  Gln
               275                      280                      285

ACA  GGC  CCA  GCC  AGA  ACT  ATT  CAA  GCC  GAT  CAA  GTT  CCA  CCA  CCT  TCG    911
Thr  Gly  Pro  Ala  Arg  Thr  Ile  Gln  Ala  Asp  Gln  Val  Pro  Pro  Pro  Ser
          290                      295                      300

AAA  TCA  GTT  CAT  CAC  GAA  GGA  AAA  AGT  CTT  TGT  CAA  GGT  ATG  AGA  AAT    959
Lys  Ser  Val  His  His  Glu  Gly  Lys  Ser  Leu  Cys  Gln  Gly  Met  Arg  Asn
     305                      310                      315

TAC  AAT  GGC  ATA  GCT  TCC  GTG  GTT  TGC  CAT  TTG  AAA  AAC  ACA  TCG  GGA   1007
Tyr  Asn  Gly  Ile  Ala  Ser  Val  Val  Cys  His  Leu  Lys  Asn  Thr  Ser  Gly
320                      325                      330                      335

GAT  GGG  AGA  AGC  CTA  TTT  GGA  ATC  GGA  TAT  AAC  TCG  TTC  ATC  ATT  ACA   1055
Asp  Gly  Arg  Ser  Leu  Phe  Gly  Ile  Gly  Tyr  Asn  Ser  Phe  Ile  Ile  Thr
                    340                      345                      350

AAC  CGA  CAT  TTG  TTC  AAA  GAA  AAT  AAT  GGT  GAA  CTT  ATA  GTG  AAA  TCC   1103
Asn  Arg  His  Leu  Phe  Lys  Glu  Asn  Asn  Gly  Glu  Leu  Ile  Val  Lys  Ser
               355                      360                      365

CAA  CAC  GGC  AAG  TTT  GTT  GTC  AAG  AAC  ACC  TCA  ACG  CTC  CGA  ATT  GCT   1151
Gln  His  Gly  Lys  Phe  Val  Val  Lys  Asn  Thr  Ser  Thr  Leu  Arg  Ile  Ala
          370                      375                      380

CCA  GTT  GGA  AAA  ACT  GAT  CTT  TTG  ATA  ATT  CGG  ATG  CCG  AAA  GAC  TTT   1199
Pro  Val  Gly  Lys  Thr  Asp  Leu  Leu  Ile  Ile  Arg  Met  Pro  Lys  Asp  Phe
     385                      390                      395

CCT  CCA  TTC  CAT  AGT  AGA  GCT  AGG  TTT  AGG  GCC  ATG  AAA  GCT  GGA  GAC   1247
Pro  Pro  Phe  His  Ser  Arg  Ala  Arg  Phe  Arg  Ala  Met  Lys  Ala  Gly  Asp
400                      405                      410                      415

AAG  GTT  TGC  ATG  ATC  GGT  GTT  GAC  TAC  CAA  GAG  AAT  CAT  ATT  GCG  AGC   1295
Lys  Val  Cys  Met  Ile  Gly  Val  Asp  Tyr  Gln  Glu  Asn  His  Ile  Ala  Ser
                    420                      425                      430

AAA  GTA  TCT  GAA  ACT  TCT  ATT  ATC  AGT  GAG  GGC  ACG  GGA  GAG  TTT  GGA   1343
Lys  Val  Ser  Glu  Thr  Ser  Ile  Ile  Ser  Glu  Gly  Thr  Gly  Glu  Phe  Gly
               435                      440                      445

TGC  CAT  TGG  ATA  TCC  ACG  AAT  GAT  GGT  GAT  TGC  GGT  AAT  CCA  CTA  GTT   1391
Cys  His  Trp  Ile  Ser  Thr  Asn  Asp  Gly  Asp  Cys  Gly  Asn  Pro  Leu  Val
          450                      455                      460

AGT  GTT  TCA  GAT  GGT  TTC  ATT  GTT  GGC  TTG  CAT  AGT  TTG  TCG  ACA  TCA   1439
Ser  Val  Ser  Asp  Gly  Phe  Ile  Val  Gly  Leu  His  Ser  Leu  Ser  Thr  Ser
     465                      470                      475

ACC  GGA  AAT  CAA  AAT  TTC  TTC  GCT  AAA  ATA  CCC  GCA  CAA  TTT  GAA  GAA   1487
Thr  Gly  Asn  Gln  Asn  Phe  Phe  Ala  Lys  Ile  Pro  Ala  Gln  Phe  Glu  Glu
480                      485                      490                      495

AAG  GTC  CTG  AGG  AAA  ATT  GAT  GAA  TTA  ACA  TGG  AGC  AAA  CAC  TGG  AGC   1535
Lys  Val  Leu  Arg  Lys  Ile  Asp  Glu  Leu  Thr  Trp  Ser  Lys  His  Trp  Ser
                    500                      505                      510

TAC  AAT  ATT  AAT  GAA  CTG  AGT  TGG  GGA  GCT  CTT  AAG  GTG  TGG  GAA  AGT   1583
Tyr  Asn  Ile  Asn  Glu  Leu  Ser  Trp  Gly  Ala  Leu  Lys  Val  Trp  Glu  Ser
               515                      520                      525

CGT  CCC  GAA  GCA  ATT  TTT  AAT  GCG  CAA  AAG  GAA  GTC  AAC  CAA  TTG  AAT   1631
Arg  Pro  Glu  Ala  Ile  Phe  Asn  Ala  Gln  Lys  Glu  Val  Asn  Gln  Leu  Asn
          530                      535                      540
```

```
GTT  TTT  GAG  CAA  AGT  GGT  AGT  CGT  TGG  CTC  TTC  GAC  AAA  TTA  CAC  GGC          1679
Val  Phe  Glu  Gln  Ser  Gly  Ser  Arg  Trp  Leu  Phe  Asp  Lys  Leu  His  Gly
545            Phe            550                      555

AAT  TTG  AAG  GGT  GTA  AGT  TCC  GCT  TCT  AGC  AAT  TTG  GTG  ACA  AAG  CAC          1727
Asn  Leu  Lys  Gly  Val  Ser  Ser  Ala  Ser  Ser  Asn  Leu  Val  Thr  Lys  His
560                      565                      570                      575

GTT  GTT  AAA  GGC  ATT  TGT  CCT  CTC  TTC  AGG  AAC  TAT  CTC  GAG  TGT  GAT          1775
Val  Val  Lys  Gly  Ile  Cys  Pro  Leu  Phe  Arg  Asn  Tyr  Leu  Glu  Cys  Asp
                    580                      585                      590

GAA  TAG       GC  CCATGG                                                                1789
Glu  *
```

( 2 ) INFORMATION FOR SEQ ID NO:2:

( i ) SEQUENCE CHARACTERISTICS:
        ( A ) LENGTH: 592 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Phe  Ser  Leu  Leu  Gly  Ile  Ile  Asn  Thr  Ile  Gln  Ser  Arg  Tyr
1                   5                   10                  15

Leu  Val  Asp  His  Ser  Val  Glu  Asn  Ile  Arg  Lys  Leu  Gln  Leu  Ala  Lys
               20                  25                  30

Ala  Gln  Ile  Gln  Gln  Leu  Glu  Ala  His  Val  Gln  Glu  Asn  Asn  Val  Gly
          35                  40                  45

Asn  Leu  Ile  Gln  Ser  Leu  Gly  Ala  Val  Arg  Ala  Val  Tyr  His  Gln  Gly
     50                  55                  60

Val  Asp  Gly  Val  Lys  His  Ile  Lys  Arg  Glu  Leu  Gly  Leu  Lys  Gly  Val
65                  70                  75                  80

Trp  Asp  Gly  Ser  Leu  Met  Ile  Lys  Asp  Arg  Ile  Val  Cys  Gly  Phe  Thr
               85                  90                  95

Met  Ala  Gly  Gly  Ala  Met  Leu  Leu  Tyr  Gln  His  Phe  Arg  Asp  Lys  Leu
          100                 105                 110

Thr  Asn  Val  His  Val  Phe  His  Gln  Gly  Phe  Ser  Ala  Arg  Gln  Arg  Gln
     115                 120                 125

Lys  Leu  Arg  Phe  Lys  Ser  Ala  Ala  Asn  Ala  Lys  Leu  Gly  Arg  Glu  Val
130                 135                 140

Tyr  Gly  Asp  Asp  Gly  Thr  Ile  Glu  His  Tyr  Phe  Gly  Glu  Ala  Tyr  Thr
145                 150                 155                 160

Lys  Lys  Gly  Asn  Lys  Lys  Gly  Lys  Met  His  Gly  Met  Gly  Val  Lys  Thr
               165                 170                 175

Arg  Lys  Phe  Val  Ala  Thr  Tyr  Gly  Phe  Lys  Pro  Glu  Asp  Tyr  Ser  Tyr
          180                 185                 190

Val  Arg  Tyr  Leu  Asp  Pro  Leu  Thr  Gly  Glu  Thr  Leu  Asp  Glu  Ser  Pro
     195                 200                 205

Gln  Thr  Asp  Ile  Ser  Met  Val  Gln  Glu  His  Phe  Gly  Asp  Ile  Arg  Ser
     210                 215                 220

Lys  Tyr  Leu  Asp  Ser  Asp  Ser  Phe  Asp  Arg  Gln  Ala  Leu  Ile  Ala  Asn
225                 230                 235                 240

Asn  Thr  Ile  Lys  Ala  Tyr  Tyr  Val  Arg  Asn  Ser  Ala  Lys  Thr  Ala  Leu
               245                 250                 255

Glu  Val  Asp  Leu  Thr  Pro  His  Asn  Pro  Leu  Lys  Val  Cys  Asp  Asn  Lys
          260                 265                 270

Leu  Thr  Ile  Ala  Gly  Phe  Pro  Asp  Arg  Glu  Ala  Glu  Leu  Arg  Gln  Thr
```

|           |     | 275 |     |     |     | 280 |     |     |     | 285 |     |     |     |
|-----------|-----|-----|-----|-----|-----|-----|-----|-----|-----|-----|-----|-----|-----|
| Gly | Pro 290 | Ala | Arg | Thr | Ile | Gln 295 | Ala | Asp | Gln | Val | Pro 300 | Pro | Ser | Lys |
| Ser 305 | Val | His | His | Glu | Gly 310 | Lys | Ser | Leu | Cys | Gln 315 | Gly | Met | Arg | Asn | Tyr 320 |
| Asn | Gly | Ile | Ala | Ser 325 | Val | Val | Cys | His | Leu 330 | Lys | Asn | Thr | Ser | Gly 335 | Asp |
| Gly | Arg | Ser | Leu 340 | Phe | Gly | Ile | Gly | Tyr 345 | Asn | Ser | Phe | Ile | Ile 350 | Thr | Asn |
| Arg | His | Leu 355 | Phe | Lys | Glu | Asn | Asn 360 | Gly | Glu | Leu | Ile | Val 365 | Lys | Ser | Gln |
| His | Gly 370 | Lys | Phe | Val | Val | Lys 375 | Asn | Thr | Ser | Thr | Leu 380 | Arg | Ile | Ala | Pro |
| Val 385 | Gly | Lys | Thr | Asp | Leu 390 | Leu | Ile | Ile | Arg | Met 395 | Pro | Lys | Asp | Phe | Pro 400 |
| Pro | Phe | His | Ser | Arg 405 | Ala | Arg | Phe | Arg | Ala 410 | Met | Lys | Ala | Gly | Asp 415 | Lys |
| Val | Cys | Met | Ile 420 | Gly | Val | Asp | Tyr | Gln 425 | Glu | Asn | His | Ile | Ala 430 | Ser | Lys |
| Val | Ser | Glu 435 | Thr | Ser | Ile | Ile | Ser 440 | Glu | Gly | Thr | Gly | Glu 445 | Phe | Gly | Cys |
| His | Trp 450 | Ile | Ser | Thr | Asn | Asp 455 | Gly | Asp | Cys | Gly | Asn 460 | Pro | Leu | Val | Ser |
| Val 465 | Ser | Asp | Gly | Phe | Ile 470 | Val | Gly | Leu | His | Ser 475 | Leu | Ser | Thr | Ser | Thr 480 |
| Gly | Asn | Gln | Asn | Phe 485 | Phe | Ala | Lys | Ile | Pro 490 | Ala | Gln | Phe | Glu | Glu 495 | Lys |
| Val | Leu | Arg | Lys 500 | Ile | Asp | Glu | Leu | Thr 505 | Trp | Ser | Lys | His | Trp 510 | Ser | Tyr |
| Asn | Ile | Asn | Glu 515 | Leu | Ser | Trp | Gly 520 | Ala | Leu | Lys | Val | Trp 525 | Glu | Ser | Arg |
| Pro | Glu 530 | Ala | Ile | Phe | Asn | Ala 535 | Gln | Lys | Glu | Val | Asn 540 | Gln | Leu | Asn | Val |
| Phe 545 | Glu | Gln | Ser | Gly | Ser 550 | Arg | Trp | Leu | Phe | Asp 555 | Lys | Leu | His | Gly | Asn 560 |
| Leu | Lys | Gly | Val | Ser 565 | Ser | Ala | Ser | Ser | Asn 570 | Leu | Val | Thr | Lys | His 575 | Val |
| Val | Lys | Gly | Ile 580 | Cys | Pro | Leu | Phe | Arg 585 | Asn | Tyr | Leu | Glu | Cys 590 | Asp | Glu |

( 2 ) INFORMATION FOR SEQ ID NO:3:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligonucleotide"

( i i i ) HYPOTHETICAL: NO ( i v ) ANTI-SENSE: NO ( x i ) SEQUENCE DESCRIPTION: SEQ ID NO:3:

GCTATGACAG AATTCACTGG CCTAACCATG GGCTTCTCTC TCC    43

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic oligonucleotide"

( i i i ) HYPOTHETICAL: NO ( i v ) ANTI-SENSE: NO ( x i ) SEQUENCE DESCRIPTION: SEQ ID NO:4:

```
CCCATAAGTG  GATCCAAGAA  ACCATGGGCC  TATTCATCAC  AC                                    42
```

( 2 ) INFORMATION FOR SEQ ID NO:5:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: PAPAYA RINGSPOT VIRUS
        ( B ) STRAIN: P-TYPE
        ( C ) INDIVIDUAL ISOLATE: USA (HA attenuated)

( i x ) FEATURE:
        ( A ) NAME/KEY: CDS
        ( B ) LOCATION: 3..1782

( i x ) FEATURE:
        ( A ) NAME/KEY: mat_peptide
        ( B ) LOCATION: 3..191

( i x ) FEATURE:
        ( A ) NAME/KEY: mat_peptide
        ( B ) LOCATION: 192..362

( i x ) FEATURE:
        ( A ) NAME/KEY: mat_peptide
        ( B ) LOCATION: 363..1643

( i x ) FEATURE:
        ( A ) NAME/KEY: mat_peptide
        ( B ) LOCATION: 1644..1782

( x i ) SEQUENCE DESCRIPTION: SEQ ID NO:5:

```
CC  ATG  GGC  TTC  TCT  CTC  CTT  GGT  GTT  ATA  AAC  ACT  ATC  CAG  AGT  AGA            47
    Met  Gly  Phe  Ser  Leu  Leu  Gly  Val  Ile  Asn  Thr  Ile  Gln  Ser  Arg
     1             5                        10                       15

TAT  CTA  GTT  GAC  CAC  TCA  GTT  GAA  AAT  ATC  AGA  AAA  CTT  CAA  CTG  GCG           95
Tyr  Leu  Val  Asp  His  Ser  Val  Glu  Asn  Ile  Arg  Lys  Leu  Gln  Leu  Ala
                    20                        25                       30

AAG  GCC  CAA  ATT  CAA  CAA  CTT  GAA  GCT  CAT  GTG  CAG  GAA  AAC  AAT  GTT          143
Lys  Ala  Gln  Ile  Gln  Gln  Leu  Glu  Ala  His  Val  Gln  Glu  Asn  Asn  Val
               35                        40                       45

GAA  AAT  TTA  ATT  CAA  TCT  CTT  GGT  GCT  GTC  AGA  GCT  GTT  TAC  CAT  CAA          191
Glu  Asn  Leu  Ile  Gln  Ser  Leu  Gly  Ala  Val  Arg  Ala  Val  Tyr  His  Gln
          50                        55                       60

AGT  GTT  GAT  GGA  TTT  AAA  CAC  ATA  AAG  CGA  GAG  TTG  GGT  TTG  AAA  GGA          239
```

-continued

| | | | | | | | | | | | | | | | | |
|---|---|---|---|---|---|---|---|---|---|---|---|---|---|---|---|---|
| | Ser | Val | Asp | Gly | Phe | Lys | His | Ile | Lys | Arg | Glu | Leu | Gly | Leu | Lys | Gly |
| | | 65 | | | | 70 | | | | | 75 | | | | | |

| GTT | TGG | GAT | GGC | TCA | TTG | ATG | ATT | AAG | GAT | GCG | ATT | GTA | TGC | GGT | TTC | 287 |
|---|---|---|---|---|---|---|---|---|---|---|---|---|---|---|---|---|
| Val | Trp | Asp | Gly | Ser | Leu | Met | Ile | Lys | Asp | Ala | Ile | Val | Cys | Gly | Phe | |
| 80 | | | | 85 | | | | | 90 | | | | | 95 | | |

| ACA | ATG | GCT | GGC | GGT | GCG | ATG | CTT | TTG | TAC | CAA | CAT | TTT | CGT | GAT | AAG | 335 |
|---|---|---|---|---|---|---|---|---|---|---|---|---|---|---|---|---|
| Thr | Met | Ala | Gly | Gly | Ala | Met | Leu | Leu | Tyr | Gln | His | Phe | Arg | Asp | Lys | |
| | | | 100 | | | | | 105 | | | | | 110 | | | |

| TTT | ACA | AAT | GTT | CAT | GTG | TTT | CAC | CAA | GGT | TTC | TCT | GCG | CGA | CAG | AGA | 383 |
|---|---|---|---|---|---|---|---|---|---|---|---|---|---|---|---|---|
| Phe | Thr | Asn | Val | His | Val | Phe | His | Gln | Gly | Phe | Ser | Ala | Arg | Gln | Arg | |
| | | | 115 | | | | 120 | | | | | 125 | | | | |

| CAA | AAG | TTA | AGA | TTT | AAG | TCA | GCA | GCG | AAT | GCT | AAG | CTT | GGT | CGA | GAG | 431 |
|---|---|---|---|---|---|---|---|---|---|---|---|---|---|---|---|---|
| Gln | Lys | Leu | Arg | Phe | Lys | Ser | Ala | Ala | Asn | Ala | Lys | Leu | Gly | Arg | Glu | |
| | | 130 | | | | | 135 | | | | 140 | | | | | |

| GTC | TAT | GGA | GAT | GAT | GGG | ACA | ATT | GAG | CAC | TAT | TTT | GGA | GAA | GCG | TAC | 479 |
|---|---|---|---|---|---|---|---|---|---|---|---|---|---|---|---|---|
| Val | Tyr | Gly | Asp | Asp | Gly | Thr | Ile | Glu | His | Tyr | Phe | Gly | Glu | Ala | Tyr | |
| | 145 | | | | | 150 | | | | | 155 | | | | | |

| ACG | AAG | AAA | GGA | AAC | AAG | AAA | GGA | AAG | ATG | CAT | GGC | ATG | GGT | GTT | AAG | 527 |
|---|---|---|---|---|---|---|---|---|---|---|---|---|---|---|---|---|
| Thr | Lys | Lys | Gly | Asn | Lys | Lys | Gly | Lys | Met | His | Gly | Met | Gly | Val | Lys | |
| 160 | | | | | 165 | | | | | 170 | | | | | 175 | |

| ACG | AGA | AAG | TTT | GTT | GCG | ACA | TAT | GGA | TTT | AAA | CCG | GAG | GAT | TAC | TCG | 575 |
|---|---|---|---|---|---|---|---|---|---|---|---|---|---|---|---|---|
| Thr | Arg | Lys | Phe | Val | Ala | Thr | Tyr | Gly | Phe | Lys | Pro | Glu | Asp | Tyr | Ser | |
| | | | | 180 | | | | | 185 | | | | | 190 | | |

| TAC | GTG | CGG | TAC | TTG | GAC | CCT | TTA | ACA | GGT | GAG | ACT | TTG | GAT | GAA | AGC | 623 |
|---|---|---|---|---|---|---|---|---|---|---|---|---|---|---|---|---|
| Tyr | Val | Arg | Tyr | Leu | Asp | Pro | Leu | Thr | Gly | Glu | Thr | Leu | Asp | Glu | Ser | |
| | | | 195 | | | | | 200 | | | | | 205 | | | |

| CCA | CAG | ACT | GAT | ATC | TCA | ATG | GTG | CAA | GAT | CAT | TTT | AGT | GAT | ATT | CGG | 671 |
|---|---|---|---|---|---|---|---|---|---|---|---|---|---|---|---|---|
| Pro | Gln | Thr | Asp | Ile | Ser | Met | Val | Gln | Asp | His | Phe | Ser | Asp | Ile | Arg | |
| | | 210 | | | | | 215 | | | | | 220 | | | | |

| AGA | AAG | TAC | ATG | GAT | TCA | GAC | AGC | TTC | GAT | AGG | CAG | GCT | TTA | ATA | GCA | 719 |
|---|---|---|---|---|---|---|---|---|---|---|---|---|---|---|---|---|
| Arg | Lys | Tyr | Met | Asp | Ser | Asp | Ser | Phe | Asp | Arg | Gln | Ala | Leu | Ile | Ala | |
| | 225 | | | | | 230 | | | | | 235 | | | | | |

| AAC | AAT | ACA | ATT | AAG | GCT | TAT | TAT | GTC | CGA | AAC | TCC | GCG | AAG | GCA | GCA | 767 |
|---|---|---|---|---|---|---|---|---|---|---|---|---|---|---|---|---|
| Asn | Asn | Thr | Ile | Lys | Ala | Tyr | Tyr | Val | Arg | Asn | Ser | Ala | Lys | Ala | Ala | |
| 240 | | | | | 245 | | | | | 250 | | | | | 255 | |

| TTG | GAA | GTC | GAT | CTG | ACA | CCG | CAC | AAC | CCT | CTC | AAA | GTT | TGT | GAC | AAT | 815 |
|---|---|---|---|---|---|---|---|---|---|---|---|---|---|---|---|---|
| Leu | Glu | Val | Asp | Leu | Thr | Pro | His | Asn | Pro | Leu | Lys | Val | Cys | Asp | Asn | |
| | | | | 260 | | | | | 265 | | | | | 270 | | |

| AAA | TTG | ACC | ATT | GCA | GGA | TTT | CCT | GAC | AGG | GAA | GCT | GAG | CTG | AGA | CAA | 863 |
|---|---|---|---|---|---|---|---|---|---|---|---|---|---|---|---|---|
| Lys | Leu | Thr | Ile | Ala | Gly | Phe | Pro | Asp | Arg | Glu | Ala | Glu | Leu | Arg | Gln | |
| | | | 275 | | | | | 280 | | | | | 285 | | | |

| ACA | GGC | CCG | CCC | AGA | ACT | ATT | CAA | GTA | GAT | CAA | GTG | CCA | CCA | CCC | TCG | 911 |
|---|---|---|---|---|---|---|---|---|---|---|---|---|---|---|---|---|
| Thr | Gly | Pro | Pro | Arg | Thr | Ile | Gln | Val | Asp | Gln | Val | Pro | Pro | Pro | Ser | |
| | | 290 | | | | | 295 | | | | | 300 | | | | |

| AAA | TCA | GTT | CAT | CAC | GAA | GGA | AAA | AGT | CTT | TGT | CAA | GGC | ATG | AGA | AAT | 959 |
|---|---|---|---|---|---|---|---|---|---|---|---|---|---|---|---|---|
| Lys | Ser | Val | His | His | Glu | Gly | Lys | Ser | Leu | Cys | Gln | Gly | Met | Arg | Asn | |
| | 305 | | | | | 310 | | | | | 315 | | | | | |

| TAC | AAT | GGC | ATA | GCT | TCT | GTG | GTT | TGC | CAT | TTG | AAA | AAC | ACA | TCA | GGA | 1007 |
|---|---|---|---|---|---|---|---|---|---|---|---|---|---|---|---|---|
| Tyr | Asn | Gly | Ile | Ala | Ser | Val | Val | Cys | His | Leu | Lys | Asn | Thr | Ser | Gly | |
| 320 | | | | | 325 | | | | | 330 | | | | | 335 | |

| AAG | GGA | AAG | AGC | TTG | TTT | GGA | ATT | GGA | TAT | AAT | TCA | TTC | ATC | ATT | ACC | 1055 |
|---|---|---|---|---|---|---|---|---|---|---|---|---|---|---|---|---|
| Lys | Gly | Lys | Ser | Leu | Phe | Gly | Ile | Gly | Tyr | Asn | Ser | Phe | Ile | Ile | Thr | |
| | | | | 340 | | | | | 345 | | | | | 350 | | |

| AAC | CGA | CAT | TTG | TTC | AAG | GAG | AAT | AAT | GGT | GAA | CTT | ATA | GTG | AAA | TCC | 1103 |
|---|---|---|---|---|---|---|---|---|---|---|---|---|---|---|---|---|
| Asn | Arg | His | Leu | Phe | Lys | Glu | Asn | Asn | Gly | Glu | Leu | Ile | Val | Lys | Ser | |
| | | | 355 | | | | | 360 | | | | | 365 | | | |

| CAA | CAC | GGT | AAG | TTT | ATT | GTC | AAG | AAC | ACC | ACA | ACA | CTC | CGA | ATT | GCT | 1151 |
|---|---|---|---|---|---|---|---|---|---|---|---|---|---|---|---|---|
| Gln | His | Gly | Lys | Phe | Ile | Val | Lys | Asn | Thr | Thr | Thr | Leu | Arg | Ile | Ala | |
| | | | 370 | | | | | 375 | | | | | 380 | | | |

| CCA | GTT | GGA | AAG | ACT | GAT | CTT | TTA | ATT | ATT | CGG | ATG | CCG | AAA | GAT | TTT | 1199 |

```
Pro  Val  Gly  Lys  Thr  Asp  Leu  Leu  Ile  Ile  Arg  Met  Pro  Lys  Asp  Phe
     385                 390                      395

CCT  CCA  TTC  CAT  AGC  AGA  GCT  AGG  TTT  AGG  GCC  ATG  AAA  GCT  GGG  GAC    1247
Pro  Pro  Phe  His  Ser  Arg  Ala  Arg  Phe  Arg  Ala  Met  Lys  Ala  Gly  Asp
400                 405                      410                      415

AAG  GTT  TGC  ATG  ATA  GGT  GTT  GAC  TAC  CAA  GAG  AAT  CAT  ATC  GCG  AGC    1295
Lys  Val  Cys  Met  Ile  Gly  Val  Asp  Tyr  Gln  Glu  Asn  His  Ile  Ala  Ser
                    420                      425                      430

AAA  GTA  TCT  GAA  ACC  TCT  ATC  ATC  AGT  GAG  GGC  ACG  GGA  GAT  TTT  GGA    1343
Lys  Val  Ser  Glu  Thr  Ser  Ile  Ile  Ser  Glu  Gly  Thr  Gly  Asp  Phe  Gly
               435                      440                      445

TGC  CAC  TGG  ATA  TCC  ACG  AAT  GAC  GGT  GAT  TGC  GGT  AAT  CCT  TTA  GTT    1391
Cys  His  Trp  Ile  Ser  Thr  Asn  Asp  Gly  Asp  Cys  Gly  Asn  Pro  Leu  Val
          450                      455                      460

AGT  GTT  TCA  GAT  GGT  TTT  ATT  GTC  GGC  TTG  CAT  AGT  TTG  TCG  ACA  TCA    1439
Ser  Val  Ser  Asp  Gly  Phe  Ile  Val  Gly  Leu  His  Ser  Leu  Ser  Thr  Ser
     465                      470                      475

ACT  GGA  GAT  CAA  AAT  TTC  TTT  GCT  AAA  ATA  CCC  GCA  CAA  TTT  GAA  GAA    1487
Thr  Gly  Asp  Gln  Asn  Phe  Phe  Ala  Lys  Ile  Pro  Ala  Gln  Phe  Glu  Glu
480                      485                      490                      495

AAG  GTC  CTT  AGG  AAG  ATT  GAT  GAT  TTA  ACT  TGG  AGC  AAA  CAC  TGG  AGC    1535
Lys  Val  Leu  Arg  Lys  Ile  Asp  Asp  Leu  Thr  Trp  Ser  Lys  His  Trp  Ser
                    500                      505                      510

TAT  AAT  ATT  AAT  GAA  CTG  AGT  TGG  GGA  GCT  CTC  AAA  GTG  TGG  GAA  AGT    1583
Tyr  Asn  Ile  Asn  Glu  Leu  Ser  Trp  Gly  Ala  Leu  Lys  Val  Trp  Glu  Ser
               515                      520                      525

CGG  CCC  GAA  GCA  ATT  TTT  AAC  GCG  CAA  AAG  GAA  GTT  AAT  CAA  TTG  AAT    1631
Arg  Pro  Glu  Ala  Ile  Phe  Asn  Ala  Gln  Lys  Glu  Val  Asn  Gln  Leu  Asn
          530                      535                      540

GTT  TTC  GAG  CAA  AGT  GGT  AGT  CGT  TGG  CTC  TTT  GAC  AAA  TTA  CAC  GGC    1679
Val  Phe  Glu  Gln  Ser  Gly  Ser  Arg  Trp  Leu  Phe  Asp  Lys  Leu  His  Gly
     545                      550                      555

AAT  TTG  AAA  GGA  GTT  AGC  TCC  GCT  CCT  AGC  AAT  TTG  GTG  ACA  AAG  CAC    1727
Asn  Leu  Lys  Gly  Val  Ser  Ser  Ala  Pro  Ser  Asn  Leu  Val  Thr  Lys  His
560                      565                      570                      575

GTT  GTT  AAA  GGA  ATT  TGT  CCT  CTT  TTC  AGG  AAC  TAT  CTC  GAG  TGT  GAT    1775
Val  Val  Lys  Gly  Ile  Cys  Pro  Leu  Phe  Arg  Asn  Tyr  Leu  Glu  Cys  Asp
                    580                      585                      590

GAA  TAG    G  CCCATGGTTG  CGCTG                                                  1797
Glu  *
```

( 2 ) INFORMATION FOR SEQ ID NO:6:

( i ) SEQUENCE CHARACTERISTICS:
        ( A ) LENGTH: 592 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Gly  Phe  Ser  Leu  Leu  Gly  Val  Ile  Asn  Thr  Ile  Gln  Ser  Arg  Tyr
 1              5                        10                      15

Leu  Val  Asp  His  Ser  Val  Glu  Asn  Ile  Arg  Lys  Leu  Gln  Leu  Ala  Lys
               20                      25                      30

Ala  Gln  Ile  Gln  Gln  Leu  Glu  Ala  His  Val  Gln  Glu  Asn  Asn  Val  Glu
          35                      40                      45

Asn  Leu  Ile  Gln  Ser  Leu  Gly  Ala  Val  Arg  Ala  Val  Tyr  His  Gln  Ser
     50                      55                      60

Val  Asp  Gly  Phe  Lys  His  Ile  Lys  Arg  Glu  Leu  Gly  Leu  Lys  Gly  Val
65                       70                      75                      80
```

```
Trp Asp Gly Ser Leu Met Ile Lys Asp Ala Ile Val Cys Gly Phe Thr
             85                  90                  95
Met Ala Gly Gly Ala Met Leu Leu Tyr Gln His Phe Arg Asp Lys Phe
            100                 105                 110
Thr Asn Val His Val Phe His Gln Gly Phe Ser Ala Arg Gln Arg Gln
            115                 120                 125
Lys Leu Arg Phe Lys Ser Ala Asn Ala Lys Leu Gly Arg Glu Val
130                 135                 140
Tyr Gly Asp Asp Gly Thr Ile Glu His Tyr Phe Gly Glu Ala Tyr Thr
145                 150                 155                 160
Lys Lys Gly Asn Lys Lys Gly Lys Met His Gly Met Gly Val Lys Thr
                165                 170                 175
Arg Lys Phe Val Ala Thr Tyr Gly Phe Lys Pro Glu Asp Tyr Ser Tyr
            180                 185                 190
Val Arg Tyr Leu Asp Pro Leu Thr Gly Glu Thr Leu Asp Glu Ser Pro
            195                 200                 205
Gln Thr Asp Ile Ser Met Val Gln Asp His Phe Ser Asp Ile Arg Arg
            210                 215                 220
Lys Tyr Met Asp Ser Asp Ser Phe Asp Arg Gln Ala Leu Ile Ala Asn
225                 230                 235                 240
Asn Thr Ile Lys Ala Tyr Tyr Val Arg Asn Ser Ala Lys Ala Leu
                245                 250                 255
Glu Val Asp Leu Thr Pro His Asn Pro Leu Lys Val Cys Asp Asn Lys
            260                 265                 270
Leu Thr Ile Ala Gly Phe Pro Asp Arg Glu Ala Glu Leu Arg Gln Thr
            275                 280                 285
Gly Pro Pro Arg Thr Ile Gln Val Asp Gln Val Pro Pro Ser Lys
290                 295                 300
Ser Val His His Glu Gly Lys Ser Leu Cys Gln Gly Met Arg Asn Tyr
305                 310                 315                 320
Asn Gly Ile Ala Ser Val Val Cys His Leu Lys Asn Thr Ser Gly Lys
                325                 330                 335
Gly Lys Ser Leu Phe Gly Ile Gly Tyr Asn Ser Phe Ile Ile Thr Asn
            340                 345                 350
Arg His Leu Phe Lys Glu Asn Asn Gly Glu Leu Ile Val Lys Ser Gln
            355                 360                 365
His Gly Lys Phe Ile Val Lys Asn Thr Thr Thr Leu Arg Ile Ala Pro
            370                 375                 380
Val Gly Lys Thr Asp Leu Leu Ile Ile Arg Met Pro Lys Asp Phe Pro
385                 390                 395                 400
Pro Phe His Ser Arg Ala Arg Phe Arg Ala Met Lys Ala Gly Asp Lys
                405                 410                 415
Val Cys Met Ile Gly Val Asp Tyr Gln Glu Asn His Ile Ala Ser Lys
            420                 425                 430
Val Ser Glu Thr Ser Ile Ile Ser Glu Gly Thr Gly Asp Phe Gly Cys
            435                 440                 445
His Trp Ile Ser Thr Asn Asp Gly Asp Cys Gly Asn Pro Leu Val Ser
            450                 455                 460
Val Ser Asp Gly Phe Ile Val Gly Leu His Ser Leu Ser Thr Ser Thr
465                 470                 475                 480
Gly Asp Gln Asn Phe Phe Ala Lys Ile Pro Ala Gln Phe Glu Glu Lys
                485                 490                 495
Val Leu Arg Lys Ile Asp Asp Leu Thr Trp Ser Lys His Trp Ser Tyr
```

```
                          500                          505                         510
Asn  Ile  Asn  Glu  Leu  Ser  Trp  Gly  Ala  Leu  Lys  Val  Trp  Glu  Ser  Arg
          515                      520                     525

Pro  Glu  Ala  Ile  Phe  Asn  Ala  Gln  Lys  Glu  Val  Asn  Gln  Leu  Asn  Val
          530                      535                     540

Phe  Glu  Gln  Ser  Gly  Ser  Arg  Trp  Leu  Phe  Asp  Lys  Leu  His  Gly  Asn
545                      550                     555                          560

Leu  Lys  Gly  Val  Ser  Ser  Ala  Pro  Ser  Asn  Leu  Val  Thr  Lys  His  Val
                    565                     570                     575

Val  Lys  Gly  Ile  Cys  Pro  Leu  Phe  Arg  Asn  Tyr  Leu  Glu  Cys  Asp  Glu
                    580                     585                     590
```

(2) INFORMATION FOR SEQ ID NO:7:

(i) SEQUENCE CHARACTERISTICS:
        (A) LENGTH: 1900 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
        (A) ORGANISM: PAPAYA RINGSPOT VIRUS
        (B) STRAIN: P-TYPE
        (C) INDIVIDUAL ISOLATE: Hawaii (ix) FEATURE:
        (A) NAME/KEY: CDS
        (B) LOCATION: 3..1900

(x) PUBLICATION INFORMATION:
        (A) AUTHORS: Yeh, SD
                  Jan, F
                  Chiang, C
                  Doong, T
                  Chen, M
                  Chung, P
                  Bau, H
        (B) TITLE: Complete nucleotide sequence and genetic
              organization of papaya ringspot virus.
        (C) JOURNAL: J. Gen. Virol.
        (D) VOLUME: 73
        (F) PAGES: 2531-
        (G) DATE: 1992

(xi) SEQUENCE DESCRIPTION: SEQ ID NO:7:

```
GC  ACT  GGC  CTA  AAC  TCT  AGC  TTC  TCT  CTC  CTT  GGT  GTT  ATA  AAC  ACT        47
    Thr  Gly  Leu  Asn  Ser  Ser  Phe  Ser  Leu  Leu  Gly  Val  Ile  Asn  Thr
         595                      600                     605

ATC  CAG  AGT  AGA  TAT  CTA  GTT  GAC  CAC  TCA  GTT  GAA  AAT  ATC  AGA  AAA        95
Ile  Gln  Ser  Arg  Tyr  Leu  Val  Asp  His  Ser  Val  Glu  Asn  Ile  Arg  Lys
610                      615                     620

CTT  CAA  CTG  GCA  AAG  GCC  CAG  ATT  CAA  CAA  CTT  GAA  GCT  CAC  ATG  CAG       143
Leu  Gln  Leu  Ala  Lys  Ala  Gln  Ile  Gln  Gln  Leu  Glu  Ala  His  Met  Gln
625                      630                     635                          640

GAA  AAC  AAT  GTT  GAA  AAT  TTA  ATT  CAA  TCT  CTT  GGT  GCT  GTA  AGA  GCT       191
Glu  Asn  Asn  Val  Glu  Asn  Leu  Ile  Gln  Ser  Leu  Gly  Ala  Val  Arg  Ala
                    645                     650                     655

GTT  TAC  CAT  CAA  AGT  GTT  GAT  GGA  TTT  AAA  CAC  ATA  AAG  CGA  GAG  TTG       239
Val  Tyr  His  Gln  Ser  Val  Asp  Gly  Phe  Lys  His  Ile  Lys  Arg  Glu  Leu
              660                     665                     670
```

-continued

| | | | | | | | | | | | | | | | | |
|---|---|---|---|---|---|---|---|---|---|---|---|---|---|---|---|---|
| GGT | TTG | AAA | GGA | GTT | TGG | GAT | GGC | TCA | TTG | ATG | ATT | AAG | GAT | GCG | ATT | 287 |
| Gly | Leu | Lys | Gly | Val | Trp | Asp | Gly | Ser | Leu | Met | Ile | Lys | Asp | Ala | Ile | |
| | | 675 | | | | 680 | | | | | 685 | | | | | |
| GTA | TGC | GGT | TTC | ACA | ATG | GCT | GGC | GGT | GCG | ATG | CTT | TTG | TAC | CAA | CAC | 335 |
| Val | Cys | Gly | Phe | Thr | Met | Ala | Gly | Gly | Ala | Met | Leu | Leu | Tyr | Gln | His | |
| | | 690 | | | | 695 | | | | 700 | | | | | | |
| TTT | CGT | GAT | AAG | TTT | ACA | AAT | GTT | CAT | GTG | TTT | CAC | CAA | GGT | TTC | TCT | 383 |
| Phe | Arg | Asp | Lys | Phe | Thr | Asn | Val | His | Val | Phe | His | Gln | Gly | Phe | Ser | |
| 705 | | | | 710 | | | | | 715 | | | | | 720 | | |
| GCG | CGA | CAG | AGA | CAA | AAG | TTA | AGA | TTT | AAG | TCA | GCA | GCG | AAT | GCT | AAG | 431 |
| Ala | Arg | Gln | Arg | Gln | Lys | Leu | Arg | Phe | Lys | Ser | Ala | Ala | Asn | Ala | Lys | |
| | | | | 725 | | | | | 730 | | | | | 735 | | |
| CTT | GGT | CGA | GAG | GTC | TAT | GGA | GAT | GAT | GGG | ACA | ATT | GAG | CAC | TAT | TTT | 479 |
| Leu | Gly | Arg | Glu | Val | Tyr | Gly | Asp | Asp | Gly | Thr | Ile | Glu | His | Tyr | Phe | |
| | | | 740 | | | | | 745 | | | | 750 | | | | |
| GGA | GAA | GCG | TAC | ACG | AAA | AAA | GGA | AAC | AAA | AAA | GGA | AAG | ATG | CAT | GGC | 527 |
| Gly | Glu | Ala | Tyr | Thr | Lys | Lys | Gly | Asn | Lys | Lys | Gly | Lys | Met | His | Gly | |
| | | | 755 | | | | | 760 | | | | | 765 | | | |
| ATG | GGT | GTT | AAG | ACG | AGA | AAG | TTT | GTT | GCG | ACA | TAT | GGA | TTT | AAA | CCG | 575 |
| Met | Gly | Val | Lys | Thr | Arg | Lys | Phe | Val | Ala | Thr | Tyr | Gly | Phe | Lys | Pro | |
| | 770 | | | | | 775 | | | | | 780 | | | | | |
| GAG | GAT | TAC | TCG | TAC | GTG | CGG | TAC | TTG | GAC | CCT | TTA | ACA | GGT | GAG | ACT | 623 |
| Glu | Asp | Tyr | Ser | Tyr | Val | Arg | Tyr | Leu | Asp | Pro | Leu | Thr | Gly | Glu | Thr | |
| 785 | | | | | 790 | | | | | 795 | | | | | 800 | |
| TTG | GAT | GAA | AGC | CCA | CAG | ACT | GAT | ATC | TCA | ATG | GTG | CAA | GAT | CAT | TTT | 671 |
| Leu | Asp | Glu | Ser | Pro | Gln | Thr | Asp | Ile | Ser | Met | Val | Gln | Asp | His | Phe | |
| | | | | 805 | | | | | 810 | | | | | 815 | | |
| AGT | GAT | ATT | CGG | AGA | AAG | TAC | ATG | GAT | TCA | GAC | AGC | TTC | GAT | AGG | CAG | 719 |
| Ser | Asp | Ile | Arg | Arg | Lys | Tyr | Met | Asp | Ser | Asp | Ser | Phe | Asp | Arg | Gln | |
| | | | 820 | | | | | 825 | | | | | 830 | | | |
| GCT | TTA | ATA | GCA | AAC | AAT | ACA | ATT | AAG | GCT | TAT | TAT | GTC | CGA | AAC | TCC | 767 |
| Ala | Leu | Ile | Ala | Asn | Asn | Thr | Ile | Lys | Ala | Tyr | Tyr | Val | Arg | Asn | Ser | |
| | | 835 | | | | | 840 | | | | | 845 | | | | |
| GCG | AAG | GCA | GCA | TTG | GAA | GTC | GAT | CTG | ACA | CCG | CAC | AAC | CCT | CTC | AAA | 815 |
| Ala | Lys | Ala | Ala | Leu | Glu | Val | Asp | Leu | Thr | Pro | His | Asn | Pro | Leu | Lys | |
| | 850 | | | | | 855 | | | | | 860 | | | | | |
| GTT | TGT | GAC | AAT | AAA | TTG | ACC | ATT | GCA | GGA | TTT | CCT | GAC | AGG | GAA | GCT | 863 |
| Val | Cys | Asp | Asn | Lys | Leu | Thr | Ile | Ala | Gly | Phe | Pro | Asp | Arg | Glu | Ala | |
| 865 | | | | | 870 | | | | | 875 | | | | | 880 | |
| GAG | CTA | AGA | CAA | ACA | GGC | CCG | CCC | AGA | ACT | ATT | CAA | GTA | GAT | CAA | GTG | 911 |
| Glu | Leu | Arg | Gln | Thr | Gly | Pro | Pro | Arg | Thr | Ile | Gln | Val | Asp | Gln | Val | |
| | | | | 885 | | | | | 890 | | | | | 895 | | |
| CCA | CCA | CCC | TCG | AAA | TCA | GTT | CAT | CAC | GAA | GGA | AAA | AGT | CTT | TGT | CAA | 959 |
| Pro | Pro | Pro | Ser | Lys | Ser | Val | His | His | Glu | Gly | Lys | Ser | Leu | Cys | Gln | |
| | | | 900 | | | | | 905 | | | | | 910 | | | |
| GGC | ATG | AGA | AAT | TAC | AAT | GGC | ATA | GCT | TCT | GTG | GTT | TGC | CAT | TTG | AAA | 1007 |
| Gly | Met | Arg | Asn | Tyr | Asn | Gly | Ile | Ala | Ser | Val | Val | Cys | His | Leu | Lys | |
| | | 915 | | | | | 920 | | | | | 925 | | | | |
| AAC | ACA | TCA | GGA | AAG | GGG | AAG | AGC | TTG | TTT | GGA | ATT | GGA | TAT | AAT | TCA | 1055 |
| Asn | Thr | Ser | Gly | Lys | Gly | Lys | Ser | Leu | Phe | Gly | Ile | Gly | Tyr | Asn | Ser | |
| | 930 | | | | | 935 | | | | | 940 | | | | | |
| TTC | ATC | ATT | ACC | AAC | CGA | CAT | TTG | TTC | AAG | GAG | AAT | AAT | GGT | GAA | CTT | 1103 |
| Phe | Ile | Ile | Thr | Asn | Arg | His | Leu | Phe | Lys | Glu | Asn | Asn | Gly | Glu | Leu | |
| 945 | | | | 950 | | | | | 955 | | | | | 960 | | |
| ATA | GTG | AAA | TCC | CAA | CAC | GGT | AAG | TTT | ATT | GTC | AAG | AAC | ACC | ACA | ACA | 1151 |
| Ile | Val | Lys | Ser | Gln | His | Gly | Lys | Phe | Ile | Val | Lys | Asn | Thr | Thr | Thr | |
| | | | | 965 | | | | | 970 | | | | | 975 | | |
| CTC | CAA | ATT | GCT | CCA | GTT | GGA | AAG | ACT | GAT | CTT | TTA | ATT | ATT | CGG | ATG | 1199 |
| Leu | Gln | Ile | Ala | Pro | Val | Gly | Lys | Thr | Asp | Leu | Leu | Ile | Ile | Arg | Met | |
| | | 980 | | | | | 985 | | | | | 990 | | | | |

| | | | | | | | | | | | | | | | | |
|---|---|---|---|---|---|---|---|---|---|---|---|---|---|---|---|---|
|CCG|AAA|GAT|TTT|CCT|CCA|TTC|CAT|AGC|AGA|GCT|AGG|TTT|AGG|GCC|ATG|1247|
|Pro|Lys|Asp|Phe|Pro|Pro|Phe|His|Ser|Arg|Ala|Arg|Phe|Arg|Ala|Met| |
| |995| | | | |1000| | | |1005| | | | | | |
|AAA|GCT|GGG|GAC|AAG|GTT|TGC|ATG|ATA|GGT|GTT|GAC|TAC|CAA|GAG|AAT|1295|
|Lys|Ala|Gly|Asp|Lys|Val|Cys|Met|Ile|Gly|Val|Asp|Tyr|Gln|Glu|Asn| |
|1010| | | | |1015| | | |1020| | | | | | | |
|CAT|ATC|GCG|AGC|AAA|GTA|TCT|GAA|ACC|TCT|ATC|ATC|AGT|GAG|GGC|ACG|1343|
|His|Ile|Ala|Ser|Lys|Val|Ser|Glu|Thr|Ser|Ile|Ile|Ser|Glu|Gly|Thr| |
|1025| | | | |1030| | | |1035| | | | | |1040| |
|GGA|GAT|TTT|GGA|TGC|CAC|TGG|ATA|TCC|ACG|AAT|GAC|GGT|GAT|TGC|GGT|1391|
|Gly|Asp|Phe|Gly|Cys|His|Trp|Ile|Ser|Thr|Asn|Asp|Gly|Asp|Cys|Gly| |
| | | | |1045| | | |1050| | | | |1055| | | |
|AAT|CCT|TTA|GTT|AGT|GTT|TCA|GAT|GGT|TTT|ATT|GTC|GGC|TTG|CAT|AGT|1439|
|Asn|Pro|Leu|Val|Ser|Val|Ser|Asp|Gly|Phe|Ile|Val|Gly|Leu|His|Ser| |
| | | |1060| | | | |1065| | | | |1070| | | |
|TTG|TCG|ACA|TCA|ACT|GGA|GAT|CAA|AAT|TTC|TTT|GCC|AAA|ATA|CCC|GCA|1487|
|Leu|Ser|Thr|Ser|Thr|Gly|Asp|Gln|Asn|Phe|Phe|Ala|Lys|Ile|Pro|Ala| |
| | |1075| | | | |1080| | | | |1085| | | | |
|CAA|TTT|GAA|GAA|AAG|GTC|CTT|AGG|AAG|ATT|GAT|GAT|TTA|ACT|TGG|AGC|1535|
|Gln|Phe|Glu|Glu|Lys|Val|Leu|Arg|Lys|Ile|Asp|Asp|Leu|Thr|Trp|Ser| |
| |1090| | | | |1095| | | | |1100| | | | | |
|AAA|CAC|TGG|AGC|TAT|AAT|ATT|AAT|GAA|CTG|AGT|TGG|GGA|GCT|CTC|AAA|1583|
|Lys|His|Trp|Ser|Tyr|Asn|Ile|Asn|Glu|Leu|Ser|Trp|Gly|Ala|Leu|Lys| |
|1105| | | | |1110| | | |1115| | | | | |1120| |
|GTG|TGG|GAA|AGT|CGG|CCC|GAA|GCA|ATT|TTT|AAC|GCA|CAA|AAG|GAA|GTT|1631|
|Val|Trp|Glu|Ser|Arg|Pro|Glu|Ala|Ile|Phe|Asn|Ala|Gln|Lys|Glu|Val| |
| | | | |1125| | | |1130| | | | |1135| | | |
|AAT|CAA|TTG|AAT|GTT|TTC|GAG|CAA|AGT|GGT|GGT|CGT|TGG|CTC|TTT|GAC|1679|
|Asn|Gln|Leu|Asn|Val|Phe|Glu|Gln|Ser|Gly|Gly|Arg|Trp|Leu|Phe|Asp| |
| | | |1140| | | | |1145| | | | |1150| | | |
|AAA|TTA|CAC|GGC|AAT|TTG|AAA|GGA|GTT|AGC|TCC|GCT|CCT|AGC|AAT|TTG|1727|
|Lys|Leu|His|Gly|Asn|Leu|Lys|Gly|Val|Ser|Ser|Ala|Pro|Ser|Asn|Leu| |
| | |1155| | | | |1160| | | | |1165| | | | |
|GTG|ACA|AAG|CAC|GTT|GTT|AAA|GGA|ATT|TGT|CCT|CTT|TTC|AGG|AAC|TAT|1775|
|Val|Thr|Lys|His|Val|Val|Lys|Gly|Ile|Cys|Pro|Leu|Phe|Arg|Asn|Tyr| |
| |1170| | | | |1175| | | | |1180| | | | | |
|CTC|GAG|TGT|GAT|GAA|GAG|GCT|AAA|GCT|TTC|TTT|AGT|CCA|CTT|ATG|GGT|1823|
|Leu|Glu|Cys|Asp|Glu|Glu|Ala|Lys|Ala|Phe|Phe|Ser|Pro|Leu|Met|Gly| |
|1185| | | | |1190| | | |1195| | | | | |1200| |
|CAC|TAC|ATG|AAG|AGT|GTT|CTG|AGC|AAG|GAA|GCG|TAC|ATT|AAG|GAT|TTA|1871|
|His|Tyr|Met|Lys|Ser|Val|Leu|Ser|Lys|Glu|Ala|Tyr|Ile|Lys|Asp|Leu| |
| | | | |1205| | | | |1210| | | | |1215| | |
|TTG|AAA|TAT|TCA|AGT|GAT|ATT|GTC|GTT| |GG| | | | | |1900|
|Leu|Lys|Tyr|Ser|Ser|Asp|Ile|Val|Val| | | | | | | | |
| | | |1220| | | | |1225| | | | | | | | |

(2) INFORMATION FOR SEQ ID NO:8:

(i) SEQUENCE CHARACTERISTICS:
        (A) LENGTH: 632 amino acids
        (B) TYPE: amino acid
        (D) TOPOLOGY: linear (ii) MOLECULE TYPE: protein (xi) SEQUENCE DESCRIPTION: SEQ ID NO:8:

| | | | | | | | | | | | | | | |
|---|---|---|---|---|---|---|---|---|---|---|---|---|---|---|
|Thr|Gly|Leu|Asn|Ser|Ser|Phe|Ser|Leu|Leu|Gly|Val|Ile|Asn|Thr|Ile|
|1| | | |5| | | | |10| | | | |15|
|Gln|Ser|Arg|Tyr|Leu|Val|Asp|His|Ser|Val|Glu|Asn|Ile|Arg|Lys|Leu|
| | | |20| | | | |25| | | | |30| | |
|Gln|Leu|Ala|Lys|Ala|Gln|Ile|Gln|Gln|Leu|Glu|Ala|His|Met|Gln|Glu|
| | |35| | | | |40| | | | |45| | | |

-continued

```
Asn  Asn  Val  Glu  Asn  Leu  Ile  Gln  Ser  Leu  Gly  Ala  Val  Arg  Ala  Val
     50                      55                      60

Tyr  His  Gln  Ser  Val  Asp  Gly  Phe  Lys  His  Ile  Lys  Arg  Glu  Leu  Gly
65                      70                      75                          80

Leu  Lys  Gly  Val  Trp  Asp  Gly  Ser  Leu  Met  Ile  Lys  Asp  Ala  Ile  Val
               85                           90                          95

Cys  Gly  Phe  Thr  Met  Ala  Gly  Gly  Ala  Met  Leu  Leu  Tyr  Gln  His  Phe
              100                          105                     110

Arg  Asp  Lys  Phe  Thr  Asn  Val  His  Val  Phe  His  Gln  Gly  Phe  Ser  Ala
          115                      120                     125

Arg  Gln  Arg  Gln  Lys  Leu  Arg  Phe  Lys  Ser  Ala  Ala  Asn  Ala  Lys  Leu
     130                      135                     140

Gly  Arg  Glu  Val  Tyr  Gly  Asp  Asp  Gly  Thr  Ile  Glu  His  Tyr  Phe  Gly
145                      150                     155                         160

Glu  Ala  Tyr  Thr  Lys  Lys  Gly  Asn  Lys  Lys  Gly  Lys  Met  His  Gly  Met
                    165                          170                    175

Gly  Val  Lys  Thr  Arg  Lys  Phe  Val  Ala  Thr  Tyr  Gly  Phe  Lys  Pro  Glu
                    180                     185                     190

Asp  Tyr  Ser  Tyr  Val  Arg  Tyr  Leu  Asp  Pro  Leu  Thr  Gly  Glu  Thr  Leu
          195                      200                     205

Asp  Glu  Ser  Pro  Gln  Thr  Asp  Ile  Ser  Met  Val  Gln  Asp  His  Phe  Ser
     210                      215                     220

Asp  Ile  Arg  Arg  Lys  Tyr  Met  Asp  Ser  Asp  Ser  Phe  Asp  Arg  Gln  Ala
225                      230                     235                         240

Leu  Ile  Ala  Asn  Asn  Thr  Ile  Lys  Ala  Tyr  Tyr  Val  Arg  Asn  Ser  Ala
                    245                     250                     255

Lys  Ala  Ala  Leu  Glu  Val  Asp  Leu  Thr  Pro  His  Asn  Pro  Leu  Lys  Val
               260                     265                     270

Cys  Asp  Asn  Lys  Leu  Thr  Ile  Ala  Gly  Phe  Pro  Asp  Arg  Glu  Ala  Glu
          275                     280                     285

Leu  Arg  Gln  Thr  Gly  Pro  Pro  Arg  Thr  Ile  Gln  Val  Asp  Gln  Val  Pro
     290                      295                     300

Pro  Pro  Ser  Lys  Ser  Val  His  His  Glu  Gly  Lys  Ser  Leu  Cys  Gln  Gly
305                      310                     315                         320

Met  Arg  Asn  Tyr  Asn  Gly  Ile  Ala  Ser  Val  Val  Cys  His  Leu  Lys  Asn
                    325                     330                     335

Thr  Ser  Gly  Lys  Gly  Lys  Ser  Leu  Phe  Gly  Ile  Gly  Tyr  Asn  Ser  Phe
               340                     345                     350

Ile  Ile  Thr  Asn  Arg  His  Leu  Phe  Lys  Glu  Asn  Asn  Gly  Glu  Leu  Ile
          355                     360                     365

Val  Lys  Ser  Gln  His  Gly  Lys  Phe  Ile  Val  Lys  Asn  Thr  Thr  Thr  Leu
     370                     375                     380

Gln  Ile  Ala  Pro  Val  Gly  Lys  Thr  Asp  Leu  Leu  Ile  Ile  Arg  Met  Pro
385                      390                     395                         400

Lys  Asp  Phe  Pro  Pro  Phe  His  Ser  Arg  Ala  Arg  Phe  Arg  Ala  Met  Lys
                    405                     410                     415

Ala  Gly  Asp  Lys  Val  Cys  Met  Ile  Gly  Val  Asp  Tyr  Gln  Glu  Asn  His
               420                     425                     430

Ile  Ala  Ser  Lys  Val  Ser  Glu  Thr  Ser  Ile  Ile  Ser  Glu  Gly  Thr  Gly
          435                     440                     445

Asp  Phe  Gly  Cys  His  Trp  Ile  Ser  Thr  Asn  Asp  Gly  Asp  Cys  Gly  Asn
     450                     455                     460

Pro  Leu  Val  Ser  Val  Ser  Asp  Gly  Phe  Ile  Val  Gly  Leu  His  Ser  Leu
```

```
465                         470                         475                         480
Ser  Thr  Ser  Thr  Gly  Asp  Gln  Asn  Phe  Phe  Ala  Lys  Ile  Pro  Ala  Gln
                    485                      490                      495
Phe  Glu  Glu  Lys  Val  Leu  Arg  Lys  Ile  Asp  Asp  Leu  Thr  Trp  Ser  Lys
               500                      505                      510
His  Trp  Ser  Tyr  Asn  Ile  Asn  Glu  Leu  Ser  Trp  Gly  Ala  Leu  Lys  Val
          515                      520                      525
Trp  Glu  Ser  Arg  Pro  Glu  Ala  Ile  Phe  Asn  Ala  Gln  Lys  Glu  Val  Asn
     530                      535                      540
Gln  Leu  Asn  Val  Phe  Glu  Gln  Ser  Gly  Gly  Arg  Trp  Leu  Phe  Asp  Lys
545                      550                      555                           560
Leu  His  Gly  Asn  Leu  Lys  Gly  Val  Ser  Ser  Ala  Pro  Ser  Asn  Leu  Val
                    565                      570                      575
Thr  Lys  His  Val  Val  Lys  Gly  Ile  Cys  Pro  Leu  Phe  Arg  Asn  Tyr  Leu
               580                      585                      590
Glu  Cys  Asp  Glu  Glu  Ala  Lys  Ala  Phe  Phe  Ser  Pro  Leu  Met  Gly  His
          595                      600                      605
Tyr  Met  Lys  Ser  Val  Leu  Ser  Lys  Glu  Ala  Tyr  Ile  Lys  Asp  Leu  Leu
     610                      615                      620
Lys  Tyr  Ser  Ser  Asp  Ile  Val  Val
625                      630
```

(2) INFORMATION FOR SEQ ID NO:9:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC OLIGONUCLEOTIDE"

(iii) HYPOTHETICAL: NO (iv) ANTI-SENSE: NO (xi) SEQUENCE DESCRIPTION: SEQ ID NO:9:

TTTACAGAAT TCCCCATGGT AAACATGGTT TCTCTGCGCG ACAGAGACAA AAGTTAA    57

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic oligonucleotide"

(iii) HYPOTHETICAL: NO (iv) ANTI-SENSE: NO (xi) SEQUENCE DESCRIPTION: SEQ ID NO:10:

TAATTTGTCG GATCCCATGG GTAGACCTAG TTGCTCGAA    39

PAPAYA RINGSPOT VIRUS PROTEASE GENE

FIELD OF THE INVENTION

This invention relates to a protease gene derived from papaya ringspot virus. More specifically, the invention relates to the genetic engineering of plants and to a method for conferring viral resistance to a plant using an expression cassette encoding papaya ringspot virus PRV FLA.83 W or PRV USA P-type (HA attenuated) protease.

BACKGROUND OF THE INVENTION

Many agriculturally important crops are susceptible to infection by plant viruses, particularly papaya ringspot virus, which can seriously damage a crop, reduce its economic value to the grower, and increase its cost to the consumer. Attempts to control or prevent infection of a crop by a plant virus such as papaya ringspot virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Potyviruses are a distinct group of plant viruses which are pathogenic to various crops, and which demonstrate cross-infectivity between plant members of different families. Generally, a potyvirus is a single-stranded RNA virus that is surrounded by a repeating protein monomer, which is termed the coat protein (CP). The majority of the potyviruses are transmitted in a nonpersistent manner by aphids. As can be seen from the wide range of crops affected by potyviruses, the host range includes such diverse families of plants as *Solanaceae, Chenopodiaceae, Gramineae, Compositae, Leguminosae, Dioscroeaceae, Cucurbitaceae*, and *Caricaceae*. Potyviruses include watermelon mosaic virus II (WMVII); zucchini yellow mosaic virus (ZYMV), potato virus Y, tobacco etch and many others.

Another potyvirus of economic significance is papaya ringspot virus (PRV). Two groups of PRV have been identified: the "P" or "papaya ringspot" type infects papayas; and the "W" or "watermelon" type infects cucurbits, e.g., squash, but it is unable to infect papaya. Thus, these two groups can be distinguished by host range differences.

The potyviruses consist of flexous, filamentous particles of dimensions approximately 780×12 nanometers. The viral particles contain a single-stranded positive polarity RNA genome containing about 10,000 nucleotides. Translation of the RNA genome of potyviruses shows that the RNA encodes a single large polyprotein of about 330 kD. This polyprotein contains several proteins; these include the coat protein, nuclear inclusion proteins NIa and NIb, cytoplasmic inclusion protein (CI), and other proteases and movement proteins (see FIG. 1). These proteins are found in the infected plant cell and form the necessary components for viral replication. One of the proteins contained in the polyprotein is a 35 kD capsid or coat protein which coats and protects the viral RNA from degradation. One of the nuclear inclusion proteins, NIb, is an RNA replicase component and is thought to have polymerase activity. CI, a second inclusion protein, is believed to participate in the replicase complex and have a helicase activity. NIa, a third inclusion protein, has a protease activity. In the course of potyvirus infection, NIa and NIb are translationally transported across the nuclear membrane into the nucleus of the infected plant cell at the later stages of infection and accumulate to high levels.

The location of the protease gene appears to be conserved in these viruses. In the tobacco etch virus, the protease cleavage site has been determined to be the dipeptide Gln-Ser, Gln-Gly, or Gln-Ala. Conservation of these dipeptides at the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. For reviews, see Fitchen et al., *Annu. Rev. Microbiol.,* 4, 739 (1993) and Wilson, *Proc. Natl. Acad. Sci. USA,* 90 3134 (1993). For papaya ringspot virus, Ling et al. (*Bio/Technology,* 9, 752 (1991)) found that transgenic tobacco plants expressing the PRV coat protein (CP) gene isolated from the PRV strain HA 5-1 (mild) showed delayed symptom development and attenuation of symptoms after infection by a number of potyviruses, including tobacco etch (TEV), potato virus Y (PVY), and pepper mottle virus (PeMV). PRV does not infect tobacco, however. Thus, PRV CP transgenic tobacco plants cannot be used to evaluate protection against PRV. Fitch et al. (*Bio/Technology,* 10 , 1466 (1992)), Gonsalves (*American J. of Bot.,* 79, 88 (1992)), and Lius et al. (91*st Annual Meeting of the American Society for Horticultural Science Hortscience,* 29, 483 (1994)) reported that four $R_o$ papaya plants made transgenic for a PRV coat protein gene taken from strain HA 5-1 (mild) displayed varying degrees of resistance against PRV infection, and one line (S55-1) appeared completely resistant to PRV. This appears to be the only papaya line that shows complete resistance to PRV infection.

Even though coat protein mediated viral resistance has proven to be useful in a variety of situations, it may not always be the most effective or desirable means for providing viral resistance. In such instances, it would be advantageous to have other methods for conferring viral resistance to plants. Expression of the protease gene (NIa) from tobacco vein mottle virus (TVMV) and potato virus Y (PVY) in transgenic plants has shown the feasibility of using protease gene constructs to produce transgenic plants protected against potyvirus infection (Maiti et al., *J. Cell. Biochem., Suppl.* 16F, 217(1992); Vardi et al., *Proc. Natl. Acad. Sci. U.S.A.,* 90, 7513 (1993); Maiti et al., *Proc. Natl. Acad. Sci. U.S.A.* 90, 6110 (1993)). Maiti et al. (1993) showed that the expression of the NIa gene of TVMV in tobacco plants rendered these plants highly resistant to TVMV challenge. In addition, Maiti et al. showed that the NIa gene expressed in these plants was proteolytically active. Vardi et al. transformed tobacco plants with PVY NIa constructs. $R_1$ progeny from two lines derived from these transformed plants were resistant to challenge with virus.

There is a continuing need for the transgenic expression of genes derived from potyviruses at levels which confer resistance to infection by these viruses.

SUMMARY OF THE INVENTION

This invention provides an isolated and purified DNA molecule that encodes the protease for the FLA83 W-type strain of papaya ringspot virus (PRV) or the protease for the PRV USA P-type (HA attenuated) strain. This invention also provides an isolated and purified DNA molecule that encodes the protease and flanking gene segments for the FLA83 W-type strain of papaya ringspot virus (PRV) or the protease and flanking gene segments for the PRV USA P-type (HA attenuated) strain. The invention also provides a chimeric expression cassette comprising at least one of these DNA molecules, a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed mRNA sequences, wherein the promoter is operably linked to the DNA molecule, and the DNA molecule is operably linked to the polyadenylation signal. Another embodiment of the invention is exemplified by the insertion of multiple virus gene expression cassettes into one purified DNA molecule, e.g., a plasmid. Preferably, these cassettes include the promoter of the 35S gene of cauliflower mosaic virus and the polyadenylation signal of the cauliflower mosaic virus 35S gene.

Also provided are bacterial cells, and transformed plant cells, containing the chimeric expression cassettes comprising the protease gene derived from the FLA.83 W-type strain of papaya ringspot virus (referred to herein as PRV FLA83 W) or from the USA P-type (HA attenuated) strain of PRV, and preferably the 35S promoter of cauliflower mosaic virus and the polyadenylation signal of the cauliflower mosaic virus 35S gene. Plants are also provided, wherein the plants comprise a plurality of transformed cells transformed with an expression cassette containing the protease gene derived from the PRV FLA83 W strain or from the USA P-type (HA attenuated) strain of PRV, and preferably the cauliflower mosaic virus 35S promoter and the polyadenylation signal of the cauliflower mosaic virus gene. Transformed plants of this invention include tobacco, corn, cucumber, peppers, potatoes, soybean, squash, and tomatoes. Especially preferred are members of the *Cucurbitaceae* (e.g., squash and cucumber) family.

Another aspect of the present invention is a method of preparing a PRV-resistant plant, such as a dicot, comprising: transforming plant cells with a chimeric expression cassette comprising a promoter functional in plant cells operably linked to a DNA molecule that encodes a protease as described above; regenerating the plant cells to provide a differentiated plant; and identifying a transformed plant that expresses the PRV protease at a level sufficient to render the plant resistant to infection by the specific strains of PRV disclosed herein.

As used herein, with respect to a DNA molecule or "gene," the phrase "isolated and purified" is defined to mean that the molecule is either extracted from its context in the viral genome by chemical means and purified and/or modified to the extent that it can be introduced into the present vectors in the appropriate orientation, i.e., sense or indecency. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, the term "heterologous" is defined to mean not identical, e.g. different in nucleotide and/or amino acid sequence, phenotype or an independent isolate. As used herein, the term "expression" is defined to mean transcription or transcription followed by translation of a particular DNA molecule. As used herein, the term "flanking gene segments" means nucleotide sequences 5' to the proteolytically derived N-terminus of the NIa coding sequence and 3' to the proteolytically derived C-terminus of the NIa coding sequence, which include about 1000 nucleotides each.

BRIEF DESCRIPTION OF THE DRAWINGS

FIG. 1. Schematic representation of the genomic organization of potyviruses.

FIG. 2. The nucleotide sequence of the nuclear inclusion body A (NIa) protease gene and flanking gene segments of PRV FLA83 W [SEQ ID NO:1]. The amino acid sequence of the encoded open reading frame is shown below the nucleotide sequence [SEQ ID NO:2]. The nucleotide sequences of oligonucleotides RMM354 [SEQ ID NO:3] and RMM355 [SEQ ID NO:4] are shown above the nucleotide sequence, at the 5' and 3' ends of the nucleotide sequence, respectively. The viral-specific sequences in RMM354 and RMM355 are homologous to sequences in PRV HA (attenuated) USA P (Quemada et al., *J. Gen. Virol.,* 71, 203 (1990)). In addition RMM354 has novel restriction endonuclease cleavage sites for EcoRI and NcoI while RMM355 has novel restriction endonuclease cleavage sites for BamHI and NcoI.

FIGS. 3A–3C. The alignment of the nucleotide sequences of the nuclear inclusion body A (NIa) and flanking gene segments from PRV isolates: HA-P (Yeh et al., *J. Gen. Virol.,* 73, 2531 (1992)) [SEQ ID NO. 7]; USA P (Quemada et al., *J. Gen. Virol.,* 71, 203 (1990) [SEQ ID NO. 8]; FLA83. Sequence alignments were generated using the UWGCG program Pileup. The dots represent either the lack of sequence information at the ends of the protease gene or gaps in homology in sequences relative to others in the alignment.

FIG. 4. The alignment of the amino acid sequences from papaya ringspot virus isolates described in FIG. 3. Sequence differences between virus strains are underlined. The predicted cylindrical inclusion (CI)/VPg, VPg/NIa, and NIa/NIb cleavage sites are shown above the aligned amino acids (Q/G and Q/S). Alignments were generated using the UWGCG Pileup program. The dots represent either the lack of sequence information at the 5' end of the protease gene or gaps in homology in sequences relative to others in the alignment.

FIGS. 5A–5C. The nucleotide sequence of the nuclear inclusion body A (NIa) protease gene and flanking gene segments of PRV USA P-type strain [SEQ ID NO:5]. The amino acid sequence of the encoded open reading frame is shown below the nucleotide sequence [SEQ ID NO:6]. The nucleotide sequences of oligonucleotides RMM354 [SEQ ID NO:3] and RMM355 [SEQ ID NO:4] are shown at the 5' and 3' ends of the nucleotide sequence, respectively.

FIG. 6. A schematic representation of the cloning strategy for FLA83 gene expression cassettes.

FIG. 7A and 7B. A schematic representation of the cloning strategy for PRV USA P-type (HA attenuated) gene expression cassettes.

FIGS. 8A and 8B. A schematic representation of the cloning strategy for PRV USA P-type (HA attenuated) gene expression cassettes with a stop codon near the 5' end of the coding sequences. Oligonucleotide primers RMM333 and RMM 334 (see FIG. 5 for nucleotide sequence of these primers [SEQ ID NO:9 and 10, respectively]) were used to amplify PRV USA P-type (HA attenuated) NIa sequences and introduce a stop codon into the 5' portion of the NIa gene.

DETAILED DESCRIPTION OF THE INVENTION

Figure 1:
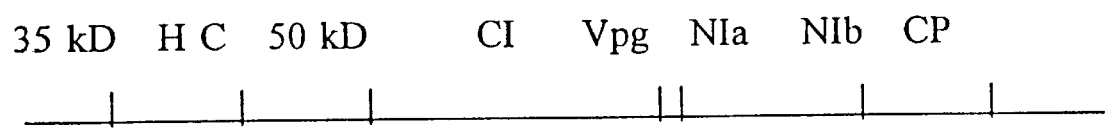

Papaya ringspot virus (PRV) is a single-stranded (+) RNA plant virus that is translated into a single polyprotein. The viral RNA genome is approximately 10,000 bases in length. The expression strategy of potyviruses includes translation of a complete polyprotein from the positive sense viral genomic RNA. Translation of the genomic RNA produces a 330 kD protein which is subsequently cleaved into at least seven smaller viral proteins by a virally encoded protease. The virally encoded proteins include a 35 kD protein at the amino terminal end of the 330 kD protein which is thought to be involved in cell to cell transmission, H C protein is 56 kD in size and is believed to be involved in insect transmission and possess proteolytic activity, a 50 kD protein, a 90 kD cylindrical inclusion protein (CI), which is part of the replicase complex and possesses helicase activity, a 6 kD VPg protein which is covalently attached to the 5' end of the viral genomic RNA, a 49 kD NIa protein which functions as a protease, a 60 kD NIb protein which functions as a polymerase, and the coat protein (36 kD).

Two types of PRV have been established based on host range. One type is designated "P type"; it infects *Caricacae* (e.g., papaya), *Cucurbitaceae* (e.g., cucurbitis), and *Chenopodiaceae* (e.g., Chenopodium) (Wang et al., *Phytopathology,* 84, 1205 (1994)). A second type is designated "W type"; it infects only *Cucurbitaceae* and *Chenopodiaceae* (Wang et al., *Phytopathology,* 84, 1205 (1994)). Isolates of the P type include HA-severe, called HA-P herein (Wang et al., *Phytopath.,* 127, 349 (1992)), HA5-1, called USA P herein, YK (Wang et al., *Phytopathology,* 84, 1205 (1994)), and other isolates as described in Tennant et al. (*Phytopathology,* 84, 1359 (1994)). Isolates of the W type include FLA83, disclosed herein, PRV-W type (Yeh et al., *Phytopathology,* 74, 1081 (1984)) and PRV-W (Aust) (Bateson et al., *Arch-Viol.,* 123, 101 (1992)).

To practice the present invention, the protease (NIa) gene of a virus must be isolated from the viral genome and inserted into a vector. Thus, the present invention provides isolated and purified DNA molecules that encode either an NIa protease of PRV FLA83 or an NIa protease of PRV USA P-type (HA attenuated). As used herein, a DNA molecule that encodes a protease gene includes nucleotides of the coding strand, also referred to as the "sense" strand, as well as nucleotides of the noncoding strand, complementary strand, also referred to as the "antisense" strand, either alone or in their base-paired configuration. For example, a DNA molecule that encodes the protease of PRV FLA83, for example, includes the DNA molecule having the nucleotide sequence of FIG. 2 [SEQ ID NO:1], a DNA molecule complementary to the nucleotide sequence of FIG. 2 [SEQ ID NO:1], as well as a DNA molecule which also encodes a PRV FLA.83 NIa protease and its complement which hybridizes with a PRV FLA83-specific DNA probe in hybridization buffer with 6XSSC, 5X Denhardt's reagent, 0.5% SDS and 100 $\mu$g/ml denatured, fragmented salmon sperm DNA and remains bound when washed at 68° C. in 0.1XSSC and 0.5% SDS (Sambrook et al., *Molecular Cloning: A Laboratory Manual,* 2nd ed. (1989)). Moreover, the DNA molecules of the present invention can include non-PRV NIa protease nucleotides that do not interfere with expression, such as the nucleotide sequences in the flanking gene segments.

The PRV protease gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate the protease gene. To do so, one having ordinary skill in the art can use information about the genomic organization of potyviruses to locate and isolate the protease gene. The protease gene is located in the 3' half of the genome, between the VPg gene and the NIb gene (FIG. 1). Additionally, the information related to proteolytic cleavage sites is used to determine the N-terminus of the protease gene. The protease recognition sites are conserved in the potyviruses and have been determined to be either the dipeptide Gln-Ser, Gln-Gly, or Gln-Ala. The nucleotide sequences which encode these dipeptides can be determined.

Using methods well known in the art, a quantity of virus is grown and harvested. The viral RNA is then separated and the protease gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the protease gene. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

Previously identified PRV NIa genes can be used as hybridization probes to screen the cDNA library to determine if any of the transformed bacteria contain DNA fragments with sequences coding for the protease region. The cDNA inserts in any bacterial colonies which contain this region can be sequenced. The protease gene is present in its entirety in colonies which have sequences that extend 5' to sequences which encode a N-terminal proteolytic cleavage site and 3' to sequences which encode a C-terminal proteolytic cleavage site for NIa.

Alternatively, cDNA fragments can be inserted in the sense orientation into expression vectors. Antibodies against the protease can be used to screen the cDNA expression library and the gene can be isolated from colonies which express the protein.

Another molecular strategy to provide virus resistance in transgenic plants is based on antisense RNA. As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited in the cell by the presense of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature,* 333:866–869 (1988)); or at a more subtle biochemical level, e.g., change in the amount of polygalacturonase and reduction in depolymerization of pectin during tomato fruit ripening (Smith et al., *Nature,* 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology", Abstract X1-022 (1994)). Thus, both antisense and sense RNA have been proven to be useful in achieving downregulation of gene expression in plants.

In the present invention, the DNA molecules encoding the protease genes of PRV FLA83 W strain and the USA P-Type (HA attenuated) strain have been determined and the genes have been inserted into expression vectors. These expression cassettes can be individually placed into a vector that can be transmitted into plants, preferably a binary vector. Alternatively, two or more of the PRV protease genes can each be present in an expression cassette which can be placed into the same binary vector, or any one of the PRV NIa expression cassettes of the present invention can be placed into a binary vector with one or more viral gene expression cassettes. The expression vectors contain the necessary genetic regulatory sequences for expression of an inserted gene. The protease gene is inserted such that those regulatory sequences are functional and the genes can be expressed when incorporated into a plant genome. For example, vectors of the present invention can contain combinations of expression cassettes that include DNA from a papaya ringspot virus (PRV) coat protein gene or a heterologous PRV protease gene (e.g., one that is from a different strain), a cucumber mosaic virus coat protein gene, a zucchini yellow mosaic virus coat protein gene, and a watermelon mosaic virus-2 coat protein gene.

Moreover, when combinations of viral gene expression cassettes are placed in the same binary plasmid, and that multigene cassette containing plasmid transformed into a plant, the multiple viral genes all preferably exhibit substantially the same degrees of efficacy when present in transgenic plants. For example, if one examines numerous transgenic lines containing two different intact viral gene expression cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the performance of each gene in these multiple gene constructs this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' Assignees' copending patent application Ser. No. 08/366,991 entitled "Transgenic Plants Expressing DNA Constructs Containing a Plurality of Genes to Impart Virus Resistance" filed on Dec. 30, 1994, incorporated by reference herein.

In order to express the viral gene, the necessary genetic regulatory sequences must be provided. Since the protease of a potyvirus is produced by the post-translational processing of a polyprotein, the protease gene isolated from viral RNA does not contain transcription and translation signals necessary for its expression once transferred and integrated into a plant genome. It must, therefore, be engineered to contain a plant expressible promoter, a translation initiation codon (ATG), and a plant functional poly(A) addition signal (AATAAA) 3' of its translation termination codon. In the present invention, the protease genes are inserted into vectors which contain cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plants or plant viruses, and can include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato may be useful.

Preferred promoters for use in the present protease-containing cassettes include the constitutive promoters from CaMV, the Ti genes nopaline synthase (Bevan et al., *Nucleic Acids Res. II,* 369 (1983)) and octopine synthase (Depicker et al., *J. Mol. Appl. Genet.,* 1, 561 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or RNAs effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity to accomplish the expression of the preselected proteins or sense and/or antisense RNAs and subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' nontranslated region which is employed is one which will cause the termination of transcription and the addition of polyadenylated ribonucleotides to the 3' end of the transcribed mRNA sequence. The termination region can be native with the promoter region, native with the structural gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of *Agrobacterium* tumor-inducing (Ti) plasmid genes, such as the nopaline synthase (NOS) gene; and (2) plant genes like the soybean 7S storage protein genes.

Preferably, the expression cassettes of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from cauliflower mosaic virus (CaMV). The poly (A) signal can be obtained from the CaMV 35S gene or from any number of well characterized plant genes, i.e., nopaline synthase, octopine synthase, and the bean storage protein gene phaseolin. The constructions are similar to that used for the expression of the CMV C coat protein in PCT Patent Application PCT/US88/04321, published on Jun. 29, 1989 as WO 89/05858, claiming the benefit of U.S. Ser. No. 135,591, filed Dec. 21, 1987, entitled "Cucumber Mosaic Virus Coat Protein Gene", and the CMV WL coat protein in PCT Patent Application PCT/US89/03288, published on Mar. 8, 1990 as WO 90/02185, claiming the benefit of U.S. Ser. No. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracyline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as *E. coli*. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For *Agrobacterium*-mediated transformation, the expression cassette will be included in a vector, and flanked by fragments of the *Agrobacterium* Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in *Agrobacterium* cells, as well as in *E. coli* cells.

All DNA manipulations are typically carried out in *E. coli* cells, and the final plasmid bearing the potyvirus gene expression cassette is moved into *Agrobacterium* cells by direct DNA transformation, conjugation, and the like. These *Agrobacterium* cells will contain a second plasmid, also derived from Ti or Ri plasmids. This second plasmid will carry all the vir genes required for transfer of the foreign DNA into plant cells. Suitable plant transformation cloning vectors include those derived from a Ti plasmid of *Agrobacterium tumefaciens*, as generally disclosed in Glassman et al. (U.S. Pat. No. 5,258,300), or *Agrobacterium rhizogenes*.

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the tumor-inducing (Ti) or root-inducing (Ri) plasmids of *Agrobacterium*, alternative methods could be used to insert the DNA constructs of the present invention into plant cells. Such methods may include, for example, the use of liposomes, electroporation, chemicals that increase the free uptake of DNA (Paszkowski et al., *EMBO J.*, 3, 2717 (1984)), microinjection (Crossway et al., *Mol. Gen. Genet.*, 202, 179 (1985)), electroporation (Fromm et al., *Proc. Natl. Acad. Sci. USA*, 82, 824 (1985)), or high-velocity microprojectiles (Klein et al., *Nature*, 327, 70 (1987) and transformation using viruses or pollen.

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation.

The transformation is carried out under conditions directed to the plant tissue of choice. The plant cells or tissue are exposed to the DNA carrying the present potyvirus multi-gene expression cassette for an effective period of time. This can range from a less-than-one-second pulse of electricity for electroporation, to a two-to-three day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to *Agrobacterium* will also include an agent inhibitory to the growth of the *Agrobacterium* cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or calli can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in a root-inducing compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity as that of the viral genomic RNA such that they are capable of base pairing with viral genornic RNA under conditions described in Chapter 7 in Sambrook et al. (1989).

The presence of a viral protease gene can also be detected by indirect assays, such as the Western blot assay described by Maiti et al. (*Proc. Natl. Acad. Sci. U.S.A.* 90, 6110 (1993)). Maiti et al. constructed a fusion protein containing the TVMV NIa protease and the *E. coli* glnH gene and transformed the construct into tobacco. Transgenic plants were assayed by Western blot analysis for the glnH gene product with an antibody to glnH. Not only was a glnH protein expressed in these plants, the glnH product was cleaved out of the fusion protein, presumably by NIa.

Potyvirus resistance can also be assayed via infectivity studies as generally disclosed by Namba et al. (*Gene,* 107, 181 (1991)) wherein plants are scored as symptomatic when any inoculated leaf shows veinclearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one are required for expression. With respect to transgenic plants of the type disclosed herein, the transgenes exhibit dominant, single gene Mendelian behavior. This genetic analysis can be part of the initial efforts to convert agronomically elite, yet sensitive lines to resistant lines. A conversion process (backcrossing) is carried out by crossing the original transgenic resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples. Enzymes were obtained from commercial sources and were used according to the vendor's recommendations or other variations known in the art. Other reagents, buffers, etc., were obtained from commercial sources, such as GIBCO-BRL, Bethesda, Md., and Sigma Chemical Co., St. Louis, Mo., unless otherwise specified.

Most of the recombinant DNA methods employed in practicing the present invention are standard procedures, well known to those skilled in the art, and described in detail in, for example, in European Patent Application Publication Number 223,452, published Nov. 29, 1986, which is incorporated herein by reference. General references containing such standard techniques include the following: R. Wu, ed., *Methods in Enzymology*, Vol. 68 (1979); J. H. Miller, *Experiments in Molecular Genetics* (1972); J. Sambrook et al., *Molecular Cloning: A Laboratory Manual*, 2nd ed. (1989); and D. M. Glover, ed., *DNA Cloning Vol. II* (1982).

Figure 6:
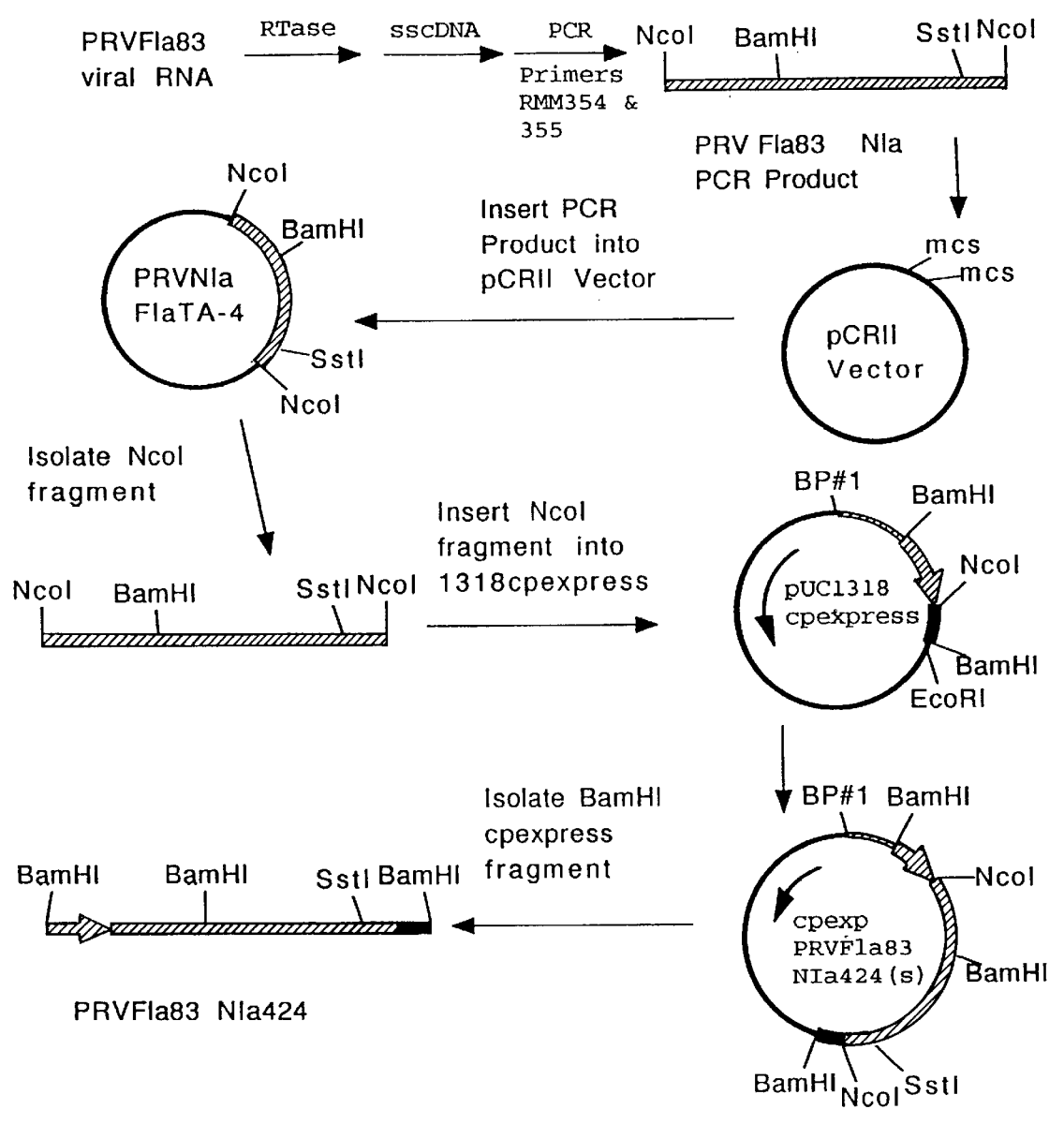
Figure 7A:
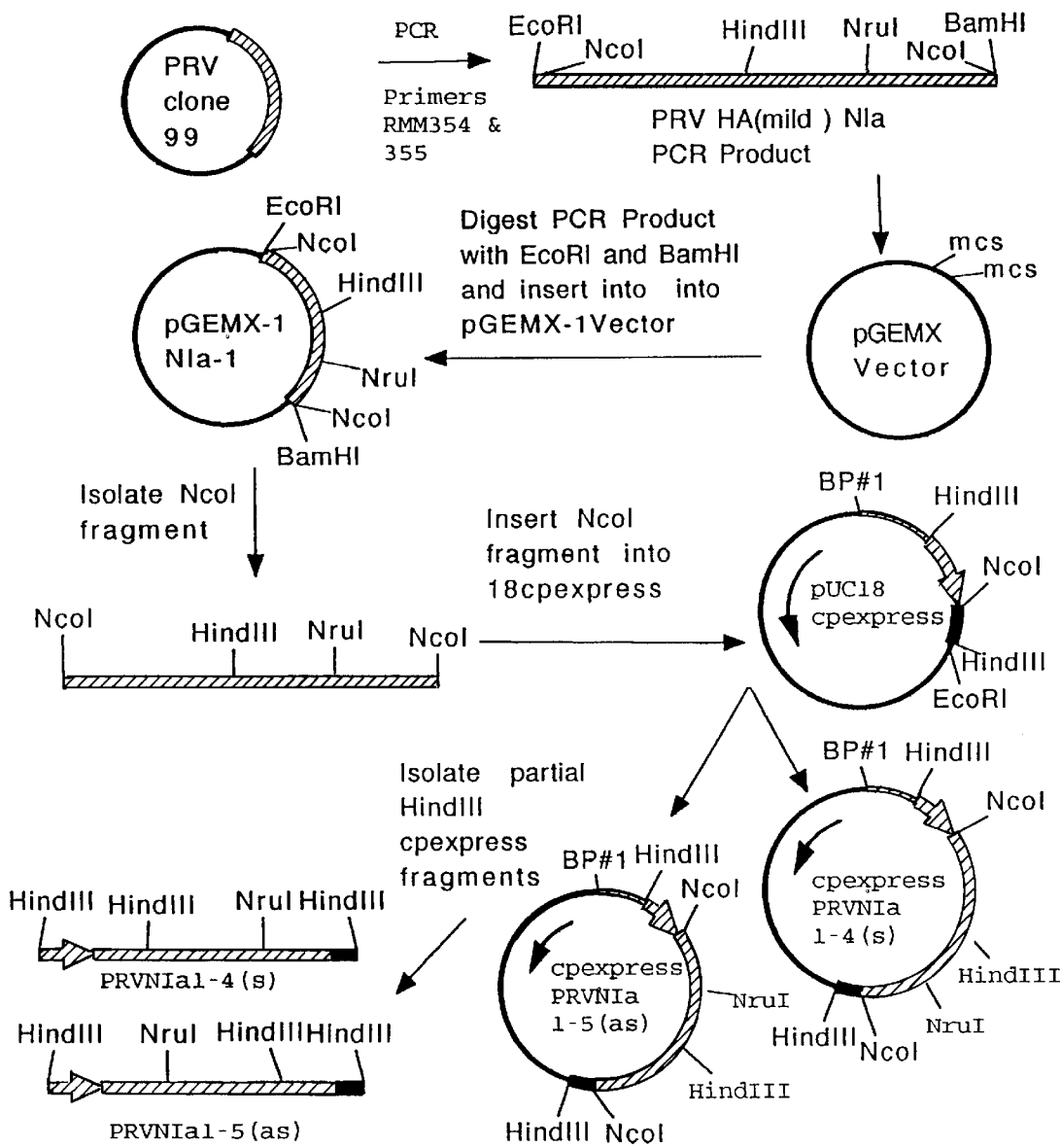
Figure 7B:
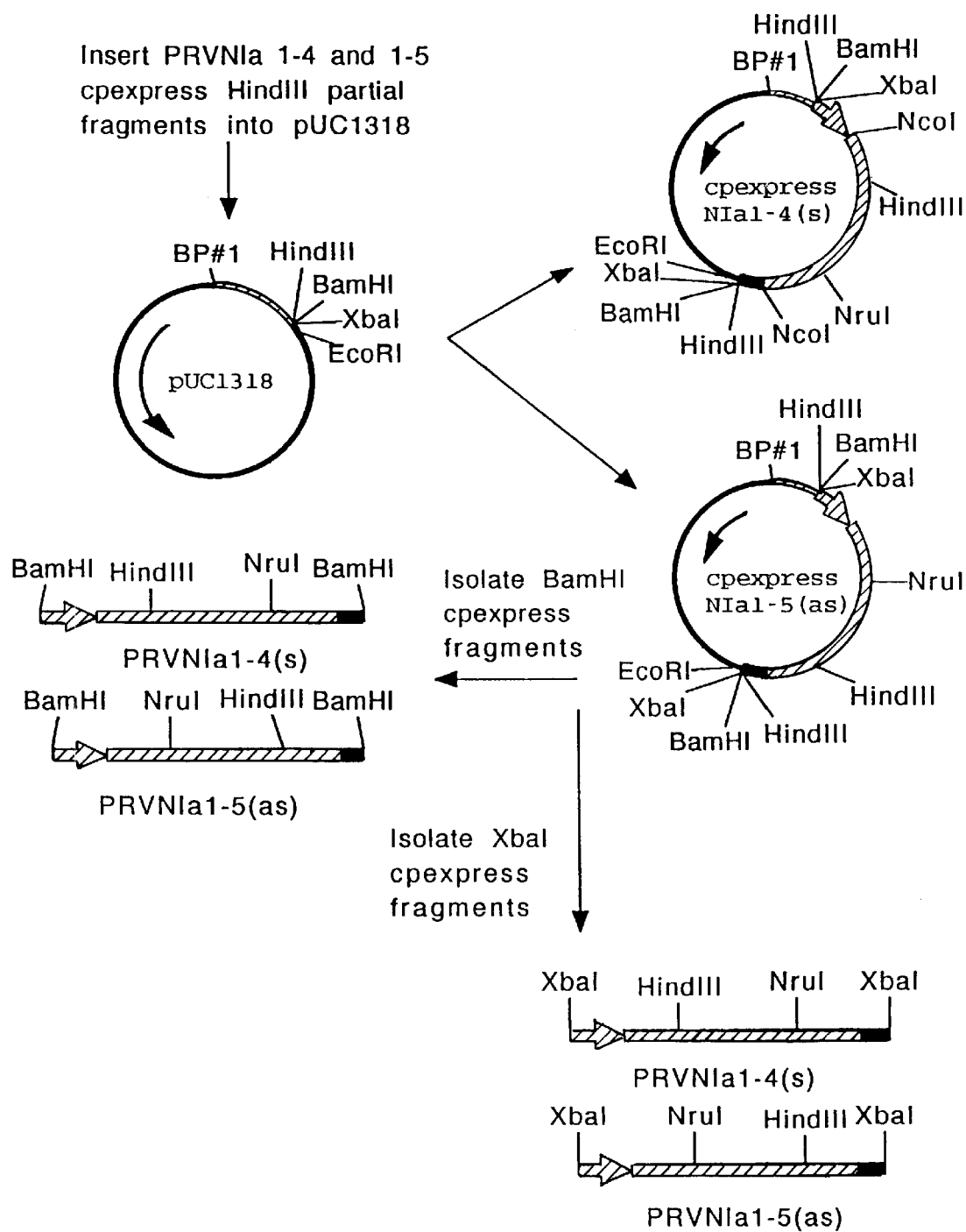
Figure 8A:
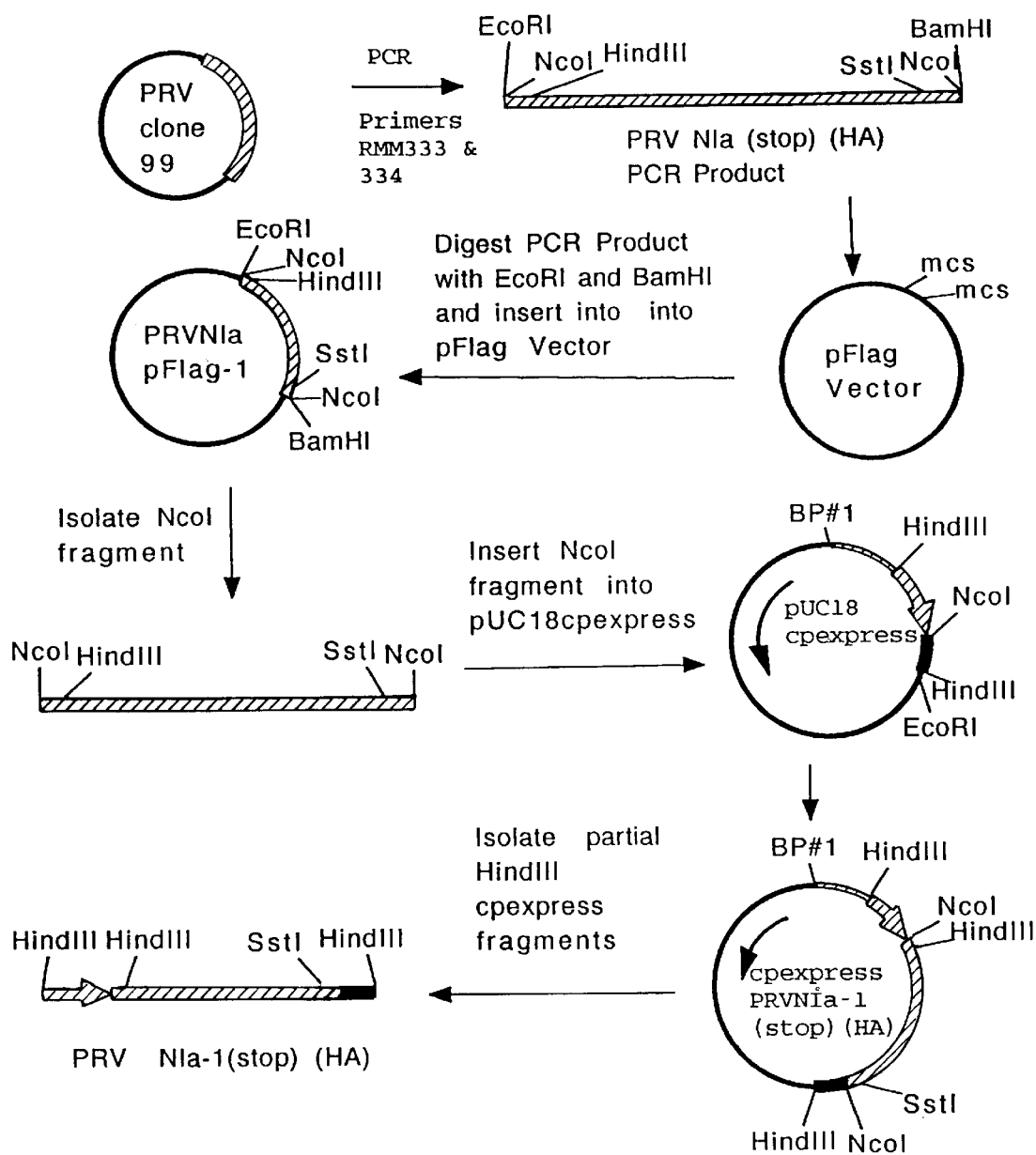

FIGS. 6–8 are presented to illustrate the constructions of this invention.

EXAMPLE I

To isolate and engineer the PRV NIa gene, the following steps can be used. 1) Purify PRV virions and isolate PRV viral RNA from the virion preparation; 2) construct single-stranded cDNAs of PRV viral RNA; 3) amplify NIa sequences by PCR amplification using viral sequence specific primers; 4) clone the PCR product into a plant expression cassette placed into an appropriate binary vector; 5) produce PRV NIa transgenic plants; and 6) challenge the progeny of $R_o$ transgenic plants to identify lines which confer the desired properties.

A. Isolation of PRV Fla83-W Viral RNA 7-day-old yellow crookneck squash plants grown in the greenhouse were inoculated with PRV strain W (watermelon) Florida-83; 21 days post inoculation leaves were harvested and PRV virus isolated. The procedure used was based on a modified method used by Purcifull et al. (*Phytopatholoy*, 69, 112 (1979)) for PRV type W isolation. Approximately 50 grams of fresh leaf tissue was homogenized in 100 ml 0.5M potassium phosphate buffer (pH 7.5 "PB") containing 0.1% sodium sulphate, 25 ml chloroform, and 25 ml carbon tetrachloride. After centrifugation of the extract at 1,000×g for 5 minutes the pellet was resuspended in 50 ml of PB buffer and centrifuged again at 1,000×g for 5 minutes. The supernatants from each centrifugation are pooled then centrifuged at 13,000×g for 15 minutes. To the resulting supernatant, Triton X-100 was added to a final concentration of 1% (v/v), polyethyleneglycol (PEG) 8,000 (Reagent grade from Sigma Chemical Co.) to a final concentration of 4% (w/v) and NaCl to a final concentration of 100 mM. The suspension was stirred for 1 hour at 0°–4° C. This suspension was centrifuged at 10,000×g for 10 minutes.

The pellet was resuspended in 40 ml of PB. After centrifugation at 12,000×g for 10 minutes the pellet was discarded and virus was precipitated from the supernatant by adding PEG to a final concentration of 8% (w/v) and NaCl to a final concentration of 100 mM, and stirring for 0.5 hour at 0°–4° C. After centrifugation at 12,000×g for 10 minutes the pellets were resuspended with the aid of a tissue grinder in 5 ml of 20 mM PB and layered over a 30% $Cs_2SO_4$ cushion. This suspension was centrifuged in a Beckman Ti75 at 140,000×g for 18 hours at 5° C. After centrifugation, the virus band was harvested and dialyzed against 20 mM PB overnight at 4° C. The dialyzed virus preparation was lysed and viral RNA precipitated by the addition of LiCl to a final concentration of 2M. The viral RNA was recovered by centrifugation. Viral RNA was dissolved and precipitated by ethanol and resuspended in water.

B. Cloning and Engineering PRV Protease Genes (a) FLA83 W

PRV FLA83 W RNA was prepared as described above. Subsequently, the first cDNA strand was synthesized using PRV FLA83 W RNA template in a reaction that included the following: approximately 3–5 μg PRV FLA83 W RNA, 1 x buffer for Superscript Reverse Transcriptase (supplied by BRL-GIBCO, Grand Island, N.Y.), 2 mM dNTPs, oligomer primer RMM355 (37.5 μg/mL, SEQ ID NO:4), 2.0 μL RNasin (Promega, Madison, Wis.), and 2.5 μL Superscript Reverse Transcriptase (BRL-GIBCO) in a 20-μL reaction. After this reaction was allowed to proceed for 30 minutes at 37° C., an aliquot of the first strand reaction was used as a template in a polymerase chain reaction with RMM354 and RMM 355 [SEQ ID NO: 3 and 4, respectively] to amplify a region of the FLA83 W genome (FIG. 6). The RMM 354 primer supplies an ATG translation initiation codon. This region includes 189 base pairs of the 3' end of the CI gene, the entire VPg gene, the entire NIa protease gene, and 146 base pairs of the 5' end of the NIb gene. The 1835 bp PCR amplified product was cloned into the pCRII vector included in the TA Cloning™ Kit supplied by Invitrogen Corp. A clone was recovered that contained PRV sequences (PRVNIaFLA TA-4). This clone was sequenced with the use of a kit (Sequenase 2 purchased from USB, Cleveland, Ohio).

The 1789 bp NcoI fragment of PRVNIaFLA TA-4 containing PRV sequences was excised from PRVNIaFLA TA-4, isolated and inserted into the plant expression cassette pUC1318cpexpress. Cassettes containing the insert of PRV sequences in the sense orientation were isolated by a partial BamHI digestion (PRVFla83 NIa424) and inserted into the BglII site of pEPG111 to give pEPG250 (for further information on parental binary vectors shown in Table 1, see Applicants' Assignees' copending patent application Ser. No. 08/366,991 entitled "Transgenic Plants Expressing DNA Constructs Containing a Plurality of Genes to Impart Virus Resistance" filed on Dec. 30, 1994, incorporated by reference herein. For further information on PRV coat protein genes, see Applicants' Assignees' copending patent application Ser. No. 08/366,881 entitled "Papaya Ringspot Virus Coat Protein Gene" filed on Dec. 30, 1994, incorporated by reference herein. For further information on ZYMV and WMV2 coat protein genes, see Applicants' Assignees copending patent application Ser. No. 08/232,846 filed on Apr. 25, 1994 entitled "Potyvirus Coat Protein Genes and Plants Transformed Therewith", incorporated by reference herein. For further information of CMV-C and CMV-wl coat protein genes, see Quemada et al., *J. Gen. Virol.*, 70, 1065 (1989). The binary plasmids were transformed into *Agrobacterium tumefaciens* strain C58Z707 and Mog301 (Table 1)

(b) USA Type P (HA attenuated)

A cDNA clone (#99) obtained from D. Gonsalves at Cornell University of the 3' end of PRV USA P-type (HA attenuated) strain served as a PCR template to amplify a PRV region that included 189 bp of the 3' end of the CI gene, the entire VpG gene, the entire NIa protease gene, and 146 bp of the 5' end of NIb gene (FIG. 5). Primers RMM354 and RMM355 [SEQ ID NO: 3 and 4, respectively] were used during the PCR amplification to introduce novel restriction sites at each end of the PRV segment engineered. The resulting PCR-amplified segment was digested with EcoRI and BamHI (see FIGS. 2 and 5) and cloned by inserting it into the vector pGEMX-1 (Promega, Madison, Wis.). The PRV sequences in a resulting clone (pGEMX-1 NIa-1) were nucleotide-sequenced (FIG. 5; [SEQ ID NO: 5]). There were no sequence differences between the sequence of clone 99 and clone pGEMX-1 NIa-1.

pGEMX-1 NIa-1 was digested with NcoI and the resulting NcoI fragment isolated for insertion into the expression cassette pUC18cpexpress. Both sense and indecency clones of expression cassettes (the expression cassettes are designated cpexpress PRV NIa 1–4 for the sense orientation and cpexpress PRV NIa 1–5 for the indecency orientation) containing the NcoI fragment of PRV were isolated. The plasmid containing the indecency orientation cassette is known as pUC18cpexpressPRVNIa1–5. The plasmid containing the sense orientation cassette is known as pUC18cpexpressPRVNIa 1–4. Subsequently, the HindIII fragments containing expression cassettes from each pUC18 plasmid containing either expression cassette were inserted into the HindIII site of pUC1318 (clone pUC1318cpexpressPRVNIa1–4 and pUC1318cpexpressPRVNIa1–5) to provide additional sites for installing cassettes into binary plasmids (FIG. 7). Subsequently, both XbaI and BamHI fragments were isolated from pUC1318cpexpressPRVNIa1–4 and pUC1318cpexpressPRVNIa1–5. These fragments were inserted into the corresponding XbaI or BglII sites of pGA482G, pEPG111, pEPG106, pEPG109, pEPG120, or pEGG252 (Table 1). Resulting binary plasmids were transformed into *Agrobacteria tumefaciens* strains Mog301 and C58Z707.

A PRV USA P-type (HA attenuated) NIa gene cassette was prepared that included an introduced stop codon (FIG. 8). To prepare the NIa coding sequence for insertion into the expression cassette pUC18cpexpress, novel restriction sites were introduced with oligomer primers RMM333 and RMM334 (see FIG. 4 [SEQ ID NO: 9 and 10, respectively]). In addition, RMM333 introduced a single base pair deletion which results in a stop codon near the translation start site. The fragment amplified by oligomer pair RMM333 and RMM334 is 1339 base pairs in length and is shown in FIG. 8. After PCR amplification, the fragment was engineered to obtain the cassette PRVNIa-1 (stop) (HA) as shown in FIG. 8. The cassette was inserted into binary plasmids as described in Table 1.

TABLE 1

| Binary | Parental Plasmid | Site | PRV NIa Cassette | pEPG# |
|---|---|---|---|---|
| pGA482G | pEPG120 (CMVwl62G) | XbaI | PRVNIa1–4 (s) (HA) | 200 |
| pGA482G | pEPG120 (CMVwl62G) | XbaI | PRVNIa1–5 (asdouble) (HA) | 201 |
| pGA482G | pGA482G | XbaI | PRVNIa1–5 (as) (HA) | 202 |
| pPRBN | pEPG109 (CWL41/Z/W) | XbaI | PRVNIa1–4 (s) (HA) | 113 |
| pPRBN | pEPG109 (CWL41/Z/W) | XbaI | PRVNIa1–5 (as) (HA) | 114 |
| pPRBN | pEPG111 (C/Z/W) | BglII | PRVNIa1–4 (s) (HA) | 224 |
| pPRBN | pEPG111 (C/Z/W) | BglII | PRVNIa1–5 (as) (HA) | 225 |
| pPRBN | pEPG106 (ZW) | BglII | PRVNIa1–4 (s) (HA) | 226 |
| pPRBN | pEPG106 (ZW) | BglII | PRVNIa1–5 (as) (HA) | 227 |

C. Transfer of PRV Protease Genes to Plants

*Agrobacterium*-mediated transfer of the plant expressible PRV protease genes described herein was done using the methods described in PCT published application WO 89/05859, entitled "*Agrobacterium* Mediated Transformation of Germinating Plant Seeds".

Transgenic cucumber lines have been produced with the USA P-type (HA-attenuated) PRV NIa gene construct described above. Progeny of $R_o$ transgenic plants were challenged in the greenhouse. Challenge results indicate that PRV USA P-type NIa transgenic $R_1$ plants are protected to a significant extent against both homologous PRV challenge and heterologous PRV challenge. Compared with non-transgenic controls, transgenic $R_1$ progeny show delayed onset and reduced symptoms on cucumber leaves and fruits.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified DNA molecule comprising essentially of DNA encoding the NIa protease of the FLA.83 W-type strain of papaya ringspot virus.

2. The isolated and purified DNA molecule of claim 1 consisting of DNA encoding the NIa protease of the FLA.83 W-type strain of papaya ringspot virus.

3. The isolated and purified DNA molecule of claim 1 from the FLA.83 W-type strain of papaya ringspot virus having the nucleotide sequence shown in SEQ ID NO: 1.

4. A vector comprising a chimeric expression cassette comprising the DNA molecule of claim 1, a promoter and a polyadenylation signal, wherein the promoter is operably linked to the DNA molecule, and the DNA molecule is operably linked to the polyadenylation signal.

5. The vector of claim 4 wherein the promoter is the cauliflower mosaic virus 35S promoter.

6. The vector of claim 5 wherein the polyadenylation signal is the polyadenylation signal of the cauliflower mosaic 35S gene.

7. A bacterial cell comprising the vector of claim 4.

8. The bacterial cell of claim 7 wherein the bacterial cell is selected from the group consisting of an *Agrobacterium tumefaciens* cell and an *Agrobacterium rhizogenes* cell.

9. A transformed plant cell transformed with the vector of claim 4.

10. The transformed plant cell of claim 9 wherein the promoter is cauliflower mosaic virus 35S promoter and the polyadenylation signal is the polyadenylation signal of the cauliflower mosaic 35S gene.

11. A plant selected from the family *Cucurbitaceae* comprising a plurality of the transformed cells of claim 10.

12. An isolated and purified DNA molecule comprising DNA encoding the NIa protease of the USA P-type (HA attenuated) strain of papaya ringspot virus.

13. The isolated and purified DNA molecule of claim 12 consisting of DNA which encodes the NIa protease of the USA P-type (HA attenuated) strain of papaya ringspot virus.

14. The isolated and purified DNA molecule of claim 12 from the USA P-type (HA attenuated) strain of papaya ringspot virus having the nucleotide sequence shown in SEQ ID NO:5.

15. A vector comprising a chimeric expression cassette comprising the DNA molecule of claim 12, a promoter and a polyadenylation signal, wherein the promoter is operably linked to the DNA molecule, and the DNA molecule is operably linked to the polyadenylation signal.

16. The vector of claim 15 wherein the promoter is the cauliflower mosaic virus 35S promoter.

17. The vector of claim 15 wherein the polyadenylation signal is the polyadenylation signal of the cauliflower mosaic 35S gene.

18. A bacterial cell comprising the vector of claim 15.

19. The bacterial cell of claim 18 wherein the bacterial cell is selected from the group consisting of an *Agrobacterium tumefaciens* cell and an *Agrobacterium rhizogenes* cell.

20. A transformed plant cell transformed with the vector of claim 15.

21. The transformed plant cell of claim 20 wherein the promoter is cauliflower mosaic virus 35S promoter and the polyadenylation signal is the polyadenylation signal of the cauliflower mosaic 35S gene.

22. A plant selected from the family *Cucurbitaceae* comprising a plurality of the transformed cells of claim 21.

23. A method of preparing a papaya ringspot viral resistant plant comprising:

(a) transforming plant cells with a chimeric expression cassette comprising a promoter functional in plant cells operably liked to a DNA molecule that encodes a protease; wherein the DNA molecule is obtained from a papaya ringspot virus strain selected from the group consisting of FLA.83 W-type and USA P-type (HA attenuated);

(b) regenerating the plant cells to provide a differentiated plant; and (c) identifying a transformed plant that expresses the papaya ringspot protease gene at a level sufficient to render the plant resistant to infection by papaya ringspot virus.

24. The method of claim 23 wherein the DNA molecule is obtained from a papaya ringspot virus strain having the nucleotide sequence show in SEQ ID NO: 1 or SEQ ID NO: 5.

25. The method of claim 23 wherein the plant is a dicot.

26. The method of claim 23 wherein the dicot is selected from the family *Cucurbitaceae.*

27. A vector comprising a chimeric expression cassette comprising the DNA molecule of claim 1 and at least one chimeric expression cassette comprising a heterologous PRV protease gene, a PRVcoat protein gene, a cucumber mosaic virus coat protein gene, a zuchini yellow mosiac virus coat protein gene, or a watermelon mosaic virus-2 coat protein gene, wherein each expression cassette comprises a promoter and a polyadenylation signal wherein the promoter is operably linked to the DNA molecule, and the DNA molecule is operably linked to the polyadenylation signal.

28. A bacterial cell comprising the vector of claim 27.

29. A transformed plant cell transformed with the vector of claim 27.

30. The transformed plant cell of claim 29 wherein the promoter is cauliflower mosaic virus 35S promoter and the polyadenylation signal is the polyadenylation signal of the cauliflower mosaic 35S gene.

31. A vector comprising a chimeric expression cassette comprising the DNA molecule of claim 12 and at least one chimeric expression cassette comprising a heterologous PRV protease gene, a PRVcoat protein gene, a cucumber mosaic virus coat protein gene, a zuchini yellow mosiac virus coat protein gene, or a watermelon mosaic virus-2 coat protein gene, wherein each expression cassette comprises a promoter and a polyadenylation signal wherein the promoter is operably linked to the DNA molecule, and the DNA molecule is operably linked to the polyadenylation signal.

32. A bacterial cell comprising the vector of claim 31.

33. A transformed plant cell transformed with the vector of claim 31.

34. The transformed plant cell of claim 33 wherein the promoter is cauliflower mosaic virus 35S promoter and the polyadenylation signal is the polyadenylation signal of the cauliflower mosaic 35S gene.

* * * * *

UNITED STATES PATENT AND TRADEMARK OFFICE
CERTIFICATE OF CORRECTION

PATENT NO.:     5,877,403
DATED :         March 2, 1999
INVENTOR(S):    McMaster *et al.*

It is hereby certified that error appear(s) in the above-identified patent and that said Letters Patent are hereby corrected as shown below:

Title page, under "Filed" please delete "Dec. 30, 1995" and insert --Dec. 30, 1994--.

In column 43, claim 1, line 2, please delete "essentially".

Signed and Sealed this

Twenty-second Day of May, 2001

*Attest:*

NICHOLAS P. GODICI

*Attesting Officer*    Acting Director of the United States Patent and Trademark Office